US011202010B2

(12) United States Patent
Takai et al.

(10) Patent No.: US 11,202,010 B2
(45) Date of Patent: Dec. 14, 2021

(54) CONTROL DEVICE, EXTERNAL DEVICE, MEDICAL OBSERVATION SYSTEM, CONTROL METHOD, DISPLAY METHOD, AND PROGRAM

(71) Applicant: Sony Olympus Medical Solutions Inc., Tokyo (JP)

(72) Inventors: Motoyuki Takai, Tokyo (JP); Masaru Sudo, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 171 days.

(21) Appl. No.: 16/492,163

(22) PCT Filed: Feb. 16, 2018

(86) PCT No.: PCT/JP2018/005568
§ 371 (c)(1),
(2) Date: Sep. 9, 2019

(87) PCT Pub. No.: WO2018/179979
PCT Pub. Date: Oct. 4, 2018

(65) Prior Publication Data
US 2021/0152747 A1    May 20, 2021

(30) Foreign Application Priority Data
Mar. 29, 2017    (JP) .............................. JP2017-064842

(51) Int. Cl.
*A61B 1/00*        (2006.01)
*G06F 3/041*       (2006.01)
(Continued)

(52) U.S. Cl.
CPC ..... *H04N 5/232933* (2018.08); *A61B 1/0005* (2013.01); *A61B 1/00006* (2013.01);
(Continued)

(58) Field of Classification Search
USPC .......................................................... 348/65
See application file for complete search history.

(56) References Cited

U.S. PATENT DOCUMENTS

2013/0016268 A1    1/2013  Nakata
2013/0229502 A1    9/2013  Kutsuma et al.
(Continued)

FOREIGN PATENT DOCUMENTS

CN    102883094 A    1/2013
CN    104382549 A    3/2015
(Continued)

OTHER PUBLICATIONS

International Search Report and Written Opinion dated May 1, 2018 for PCT/JP2018/005568 filed on Feb. 16, 2018, 11 pages including English Translation of the International Search Report.
(Continued)

*Primary Examiner* — Patricia I Young
(74) *Attorney, Agent, or Firm* — Xsensus LLP

(57) ABSTRACT

A control device, an external device, a medical observation system, a control method, a display method, and a program capable of performing predetermined processing to a position desired by an operator even under a situation where the operator's hand is not available. A control device includes: an image processing unit that processes an image signal generated by an imaging unit to generate a display image for display; a transmission/reception unit that transmits the display image generated by the image processing unit to a display device and an external device, which has a display function and is capable of bidirectional communication and receives an instruction signal including at least a position of the display image transmitted from the external device; and a control unit that executes predetermined processing on a
(Continued)

touch position of the display image according to the instruction signal from the external device.

18 Claims, 25 Drawing Sheets

(51) Int. Cl.
*G06F 3/048* (2013.01)
*H04N 5/38* (2006.01)
*H04N 5/232* (2006.01)
*A61B 1/005* (2006.01)
*G06F 3/0484* (2013.01)
*G06F 3/0488* (2013.01)
*H04N 7/18* (2006.01)
*H04N 5/225* (2006.01)

(52) U.S. Cl.
CPC ...... *A61B 1/00009* (2013.01); *A61B 1/00039* (2013.01); *A61B 1/0051* (2013.01); *A61B 1/00188* (2013.01); *G06F 3/041* (2013.01); *G06F 3/0488* (2013.01); *G06F 3/04845* (2013.01); *H04N 5/23296* (2013.01); *H04N 5/38* (2013.01); *H04N 7/183* (2013.01); *G06F 2203/04806* (2013.01); *G06F 2203/04808* (2013.01); *H04N 2005/2255* (2013.01)

(56) References Cited

U.S. PATENT DOCUMENTS

| | | | |
|---|---|---|---|
| 2015/0273324 A1* | 10/2015 | Yamamoto | A63F 13/426 463/36 |
| 2016/0331213 A1 | 11/2016 | Kim | |
| 2017/0202432 A1* | 7/2017 | Michihata | A61B 1/00006 |

FOREIGN PATENT DOCUMENTS

| | | |
|---|---|---|
| CN | 104679394 A | 6/2015 |
| CN | 105828694 A | 8/2016 |
| JP | 2008-99874 A | 5/2008 |
| JP | 2011-24901 A | 2/2011 |
| JP | 2011-152302 A | 8/2011 |
| JP | 2011-212150 A | 10/2011 |
| JP | 2011-217332 A | 10/2011 |
| JP | 2012-90785 A | 5/2012 |
| JP | 2013-248119 A | 12/2013 |
| JP | 2016-214637 A | 12/2016 |
| JP | 2017-568 A | 1/2017 |
| JP | 2017-26721 A | 2/2017 |

OTHER PUBLICATIONS

Extended European Search Report dated Feb. 20, 2020, issued in corresponding European Patent Application No. 18775816.4.

* cited by examiner

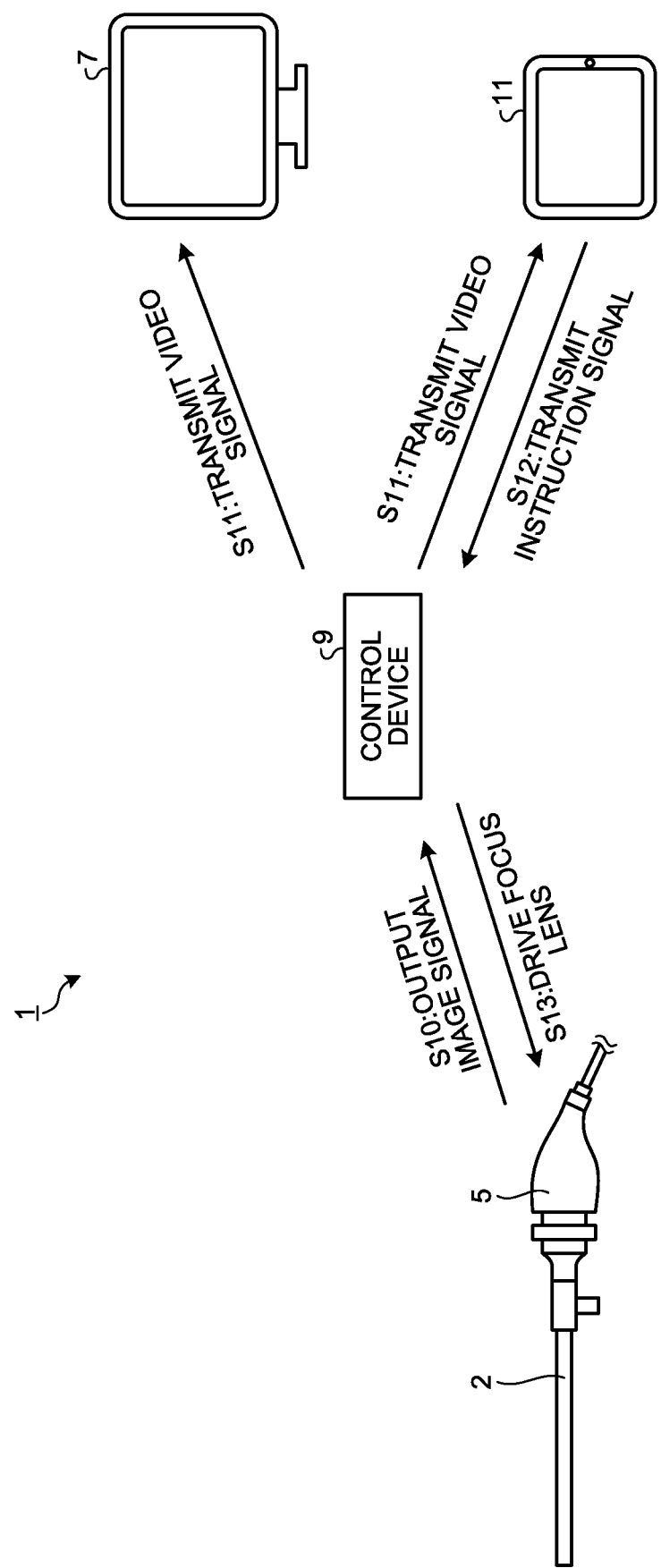

CONTROL DEVICE, EXTERNAL DEVICE, MEDICAL OBSERVATION SYSTEM, CONTROL METHOD, DISPLAY METHOD, AND PROGRAM

CROSS-REFERENCE TO RELATED APPLICATIONS

The present application is based on PCT filing PCT/JP2018/005568, filed Feb. 16, 2018, which claims priority to JP 2017-064842, filed Mar. 29, 2017, the entire contents of each are incorporated herein by reference.

TECHNICAL FIELD

The present invention relates to a control device, an external device, a medical observation system, a control method, a display method, and a program for imaging a subject and processing image data of the subject.

BACKGROUND ART

Conventionally, in an endoscope, there is known a technique capable of performing an auto focus (AF) process of automatically adjusting a focus (see Patent Literature 1). In this technique, focusing evaluation is calculated based on an imaging signal generated by an imaging unit, and drive of a focus mechanism is controlled according to the calculation result such that a central area of an image corresponding to the imaging signal is focused.

CITATION LIST

Patent Literature

Patent Literature 1: JP 2017-568 A

DISCLOSURE OF INVENTION

Technical Problem

However, a processing-compatible area is fixed to the central area in Patent Literature 1 described above. Thus, operators of the endoscope such as doctors and scopists need to move the endoscope such that a position to be desirably processed is at the center of a display monitor when desiring to perform various processes that can be executed by the endoscope, in addition to the central area of the display image displayed on the display monitor during treatment on a patient, and thus, there is a problem that an operation becomes complicated such as temporarily placing a treatment tool such as forceps or a high-frequency knife gripped by the operator in another place.

A technique of the present disclosure has been made in view of the above description, and an object thereof is to provide a control device, an external device, a medical observation system, a control method, a display method, and a program capable of performing predetermined processing to a position desired by an operator even under a situation where the operator's hand is not available.

Solution to Problem

To solve the above-described problem and achieve the object, a control device according to the present disclosure includes: an image processing unit configured to process an image signal generated by an imaging unit to generate a display image for display; a video output unit configured to output the display image generated by the image processing unit to a display device; a transmission/reception unit configured to transmit the display image generated by the image processing unit to an external device, which has a display function and is capable of bidirectional communication, and receive an instruction signal including at least one touch position in the display image from the external device; and a control unit configured to execute predetermined processing on the touch position of the display image according to the instruction signal.

Moreover, the above-described control device according to the present disclosure further includes an electronic zoom unit configured to generate an enlarged image by performing enlargement processing to cut out and enlarge a predetermined area in the display image, wherein the control unit is configured to cause the electronic zoom unit to perform the enlargement processing on an area including the touch position to generate the enlarged image, and cause the video output unit to output the enlarged image to the display device.

Moreover, in the above-described control device according to the present disclosure, the control unit includes: a determination unit configured to determine whether the area including the touch position cut out by the electronic zoom unit is a predetermined resolution or higher; and a zoom control unit configured to change an area to be cut out by the electronic zoom unit so as to include the touch position in the display image when the determination unit determines that the area including the touch position is not the predetermined resolution or higher.

Moreover, in the above-described control device according to the present disclosure, the instruction signal further includes two of the touch positions different from each other, and the zoom control unit is configured to change a size of an area to be cut out by the electronic zoom unit according to a distance between the two touch positions different from each other.

Moreover, in the above-described control device according to the present disclosure, effective number of pixels of the imaging unit is eight megapixels or more, the display device has a monitor size of 31 inches or more, and the electronic zoom unit is configured to generate the enlarged image to satisfy a resolution of two megapixels or more.

Moreover, in the above-described control device according to the present disclosure, the instruction signal further includes trajectory information of the touch position moving with a lapse of time, the display image includes a subject image and a mask area other than the subject image, and the control unit is configured to cause the video output unit to change a display position of the subject image based on the trajectory information and output the subject image to the display device.

Moreover, the above-described control device according to the present disclosure further includes an electronic zoom unit configured to generate an enlarged image by performing enlargement processing to cut out and enlarge a predetermined area in the display image, wherein the control unit is configured to cause the electronic zoom unit to perform the enlargement processing on an area of the subject image including the touch position to generate the enlarged image, and cause the video output unit to output the enlarged image to the display device.

Moreover, in the above-described control device according to the present disclosure, the control unit is configured to control drive of a lens unit having a focus mechanism, which is capable of adjusting a focus by moving one or more lenses, to cause the lens unit to be focused at a position of the display image according to the instruction signal.

Moreover, in the above-described control device according to the present disclosure, the control unit is configured to control drive of a bending unit in an endoscope, which includes a distal end portion provided with the imaging unit and a bending unit capable of bending the distal end portion in vertical and horizontal directions to bend the distal end portion toward a position of the display device according to the instruction signal.

Moreover, in the above-described control device according to the present disclosure, the control unit is configured to control drive of a support unit, the support unit being configured to hold at least the imaging unit and movably support the imaging unit, to cause a center of an imaging field of view in the imaging unit to be directed to the touch position of the display image according to the instruction signal.

Moreover, an external device according to the present disclosure includes: a display unit configured to display a display image corresponding to an image signal transmitted from a control device; a touch panel provided on a display area of the display unit in a superimposed manner, and configured to detect a touch position at which an external object comes in contact, and output an instruction signal including the touch position; and a display control unit configured to display area information indicating an area, which includes the touch position and satisfies a predetermined resolution, on the display unit to be superimposed on the display image based on the instruction signal output from the touch panel.

Moreover, the above-described external device according to the present disclosure further includes a determination unit configured to determine whether the area including the touch position is a predetermined resolution or higher, wherein the display control unit is configured to change a superimposed position of the area information so as to include the touch position when the determination unit determines that the area including the touch position is not the predetermined resolution or higher, and display the area information on the display unit.

Moreover, a medical observation system according to the present disclosure includes: an image processing unit configured to process an image signal generated by an imaging unit to generate a display image for display; a video output unit configured to output the display image generated by the image processing unit to a display device;

a transmission/reception unit that is capable of transmitting the display image and receiving information from an outside; an external device including: a display unit configured to display the display image transmitted from the transmission/reception unit; and a touch panel provided to be superimposed on a display area of the display unit, configured to detect touch positions at which an external object comes in contact, and output an instruction signal including at least one of the touch positions; and a control unit configured to execute predetermined processing on the touch position of the display image according to the instruction signal.

Moreover, a control method according to the present disclosure includes: an image processing step of processing an image signal generated by an imaging unit to generate a display image for display; a transmission step of transmitting the display image generated in the image processing step to each of a display device and an external device which has a display function and is capable of bidirectional communication; a reception step of receiving an instruction signal including at least one touch position in the display image from the external device; and a control step of executing predetermined processing on the touch position of the display image according to the instruction signal.

Moreover, a display method according to the present disclosure, executed by an external device including: a display unit that displays a display image corresponding to an image signal transmitted from a control device; and a touch panel that is provided on a display area of the display unit in a superimposed manner, detects a touch position at which an external object comes in contact, and outputs an instruction signal including the touch position, includes a display control step of displaying area information indicating an area, which includes the touch position and satisfies a predetermined resolution, on the display unit to be superimposed on the display image based on the instruction signal output from the touch panel.

Moreover, a program according to the present disclosure causes a control device to execute: an image processing step of processing an image signal generated by an imaging unit to generate a display image for display; a transmission step of transmitting the display image generated in the image processing step to each of a display device and an external device which has a display function and is capable of bidirectional communication; a reception step of receiving an instruction signal including at least one touch position in the display image from the external device; and a control step of executing predetermined processing on the touch position of the display image according to the instruction signal.

Moreover, a program according to the present disclosure causes an external device, which includes: a display unit that displays a display image corresponding to an image signal transmitted from a control device; and a touch panel that is provided on a display area of the display unit in a superimposed manner, detects a touch position at which an external object comes in contact, and outputs an instruction signal including the touch position, to execute a display control step of displaying area information indicating an area, which includes the touch position and satisfies a predetermined resolution, on the display unit to be superimposed on the display image based on the instruction signal output from the touch panel.

Advantageous Effects of Invention

According to the present disclosure, it is possible to perform the predetermined processing on the position desired by the operator even under the situation where the operator's hand is not available.

BRIEF DESCRIPTION OF DRAWINGS

FIG. 15 is a diagram illustrating an outline of processing to be executed by a medical observation system according to a second embodiment.

BEST MODE FOR CARRYING OUT THE INVENTION

Hereinafter, modes for carrying out the present invention (hereinafter, referred to as "embodiments") will be described in detail with reference to the drawings. Incidentally, the present invention is not limited by the following embodiments. In addition, the respective drawings referred to in the following description merely illustrate shapes, sizes, and positional relationships in a schematic manner to such an extent that contents of the present invention can be understood. That is, the present invention is not limited to only the shapes, sizes, and positional relationships illustrated in the respective drawings.

First Embodiment

[Schematic Configuration of Medical Observation System]

Figure 1:
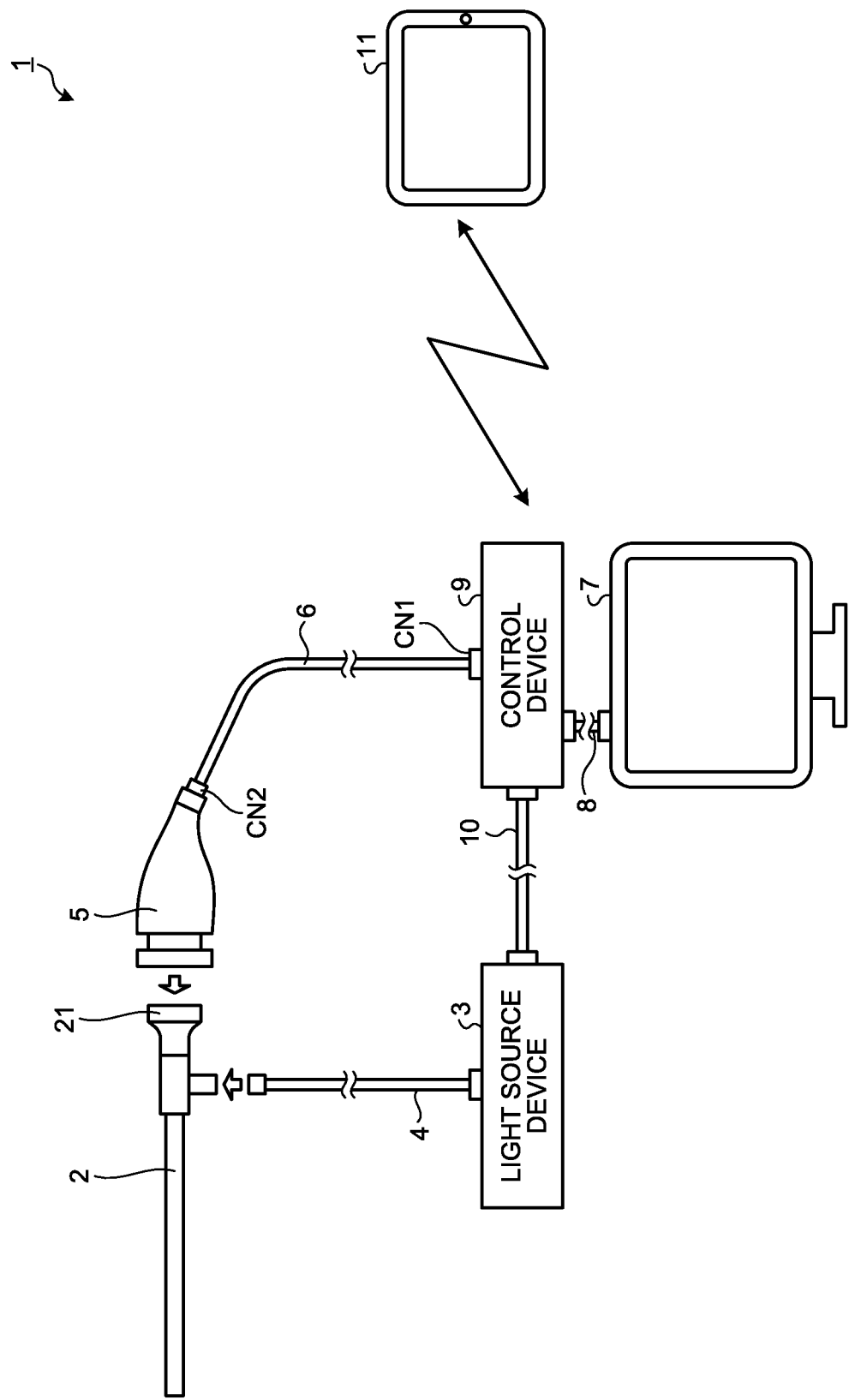
FIG. 1 is a diagram illustrating a schematic configuration of a medical observation system according to a first embodiment.

FIG. 1 is a diagram illustrating a schematic configuration of a medical observation system according to a first embodiment.

A medical observation system 1 illustrated in FIG. 1 is a device used in the medical field to capture the inside of a subject such as a living body. Incidentally, a rigid endoscope system using a rigid endoscope (insertion section 2) illustrated in FIG. 1 is described as the medical observation system 1 in the first embodiment, but the medical observation system 1 is not limited thereto, and may be a flexible endoscope system.

As illustrated in FIG. 1, the medical observation system 1 includes the insertion section 2, a light source device 3, a light guide 4, a camera head 5 (endoscopic imaging device), a first transmission cable 6, a display device 7, a second transmission cable 8, a control device 9, a third transmission cable 10, and an external device 11.

The insertion section 2 is rigid or at least partially flexible and has an elongated shape, and is inserted into a subject such as a patient. An optical system, which is configured using one or a plurality of lenses and forms an observation image, is provided inside the insertion section 2.

One end of the light guide 4 is connected with the light source device 3, and the light source device 3 emits (provides) light to illuminate the inside of the subject to the one end of the light guide 4 under control of the control device 9.

The one end of the light guide 4 is detachably connected with the light source device 3, and the other end thereof is detachably to the insertion section 2. The light guide 4 transmits the light supplied from the light source device 3 from the one end to the other end, and supplies the light to the insertion section 2.

An eyepiece section 21 of the insertion section 2 is detachably connected with the camera head 5. The camera head 5 captures a subject image (observation image) formed by the insertion section 2 under the control of the control device 9 to generate an image signal, and converts the image signal into an electric signal or an optical signal and outputs the converted signal.

One end of the first transmission cable 6 is detachably connected with the control device 9 via a connector CN1, and the other end thereof is connected with the camera head 5 via a connector CN2. The first transmission cable 6 transmits the image signal output from the camera head 5 to the control device 9, and transmits each of a control signal output from the control device 9, a synchronization signal, a clock signal, power, and the like, to the camera head 5.

Under the control of the control device 9, the display device 7 displays an observation image based on a video signal processed by the control device 9 and various types of information regarding the medical observation system 1. The display device 7 is configured using liquid crystal, organic electro luminescence (EL), or the like. In addition, the display device 7 has a monitor size of 31 inches or more, and preferably 55 inches or more. Incidentally, the display device 7 is configured with the monitor size of 31 inches or more in the first embodiment, but is not limited thereto, and may be configured with other monitor sizes. Any monitor size may be used if the monitor size is capable of displaying an image, for example, having a resolution of two megapixels (for example, a so-called 2K resolution of 1920×1080 pixels) or higher, preferably a resolution of eight megapixels (for example, a so-called 4K resolution of 3840×2160 pixels) or higher, and more preferably, a resolution of 32 megapixels (for example, a so-called 8K resolution of 7680× 4320 pixels) or higher.

One end of the second transmission cable 8 is detachably connected with the display device 7, and the other end thereof is detachably connected with the control device 9. The second transmission cable 8 transmits the video signal processed by the control device 9 to the display device 7.

The control device 9 includes a central processing unit (CPU), various memories, and the like, and integrally controls operations of the light source device 3, the camera head 5, and the display device 7 via each of the first transmission cable 6, the second transmission cable 8, and the third transmission cable 10 according to a program recorded in a memory (not illustrated). In addition, the control device 9 bidirectionally communicates various types of information with the external device 11 according to a predetermined wireless communication standard.

One end of the third transmission cable 10 is detachably connected with the light source device 3, and the other end thereof is detachably connected with the control device 9. The third transmission cable 10 transmits the control signal from the control device 9 to the light source device 3.

The external device 11 receives and displays the video signal transmitted from the control device 9, and transmits various types of information input according to user's operations to the control device 9. The external device 11 is realized using a device such as a mobile terminal and a mobile phone, an external monitor that can receive the user's operation, or the like. Incidentally, the example in which the external device 11 and the control device 9 perform the bidirectional communication in a wireless manner is described in the first embodiment, but the invention is not limited thereto, and the bidirectional communication may be performed in a wired manner.

Figure 2:
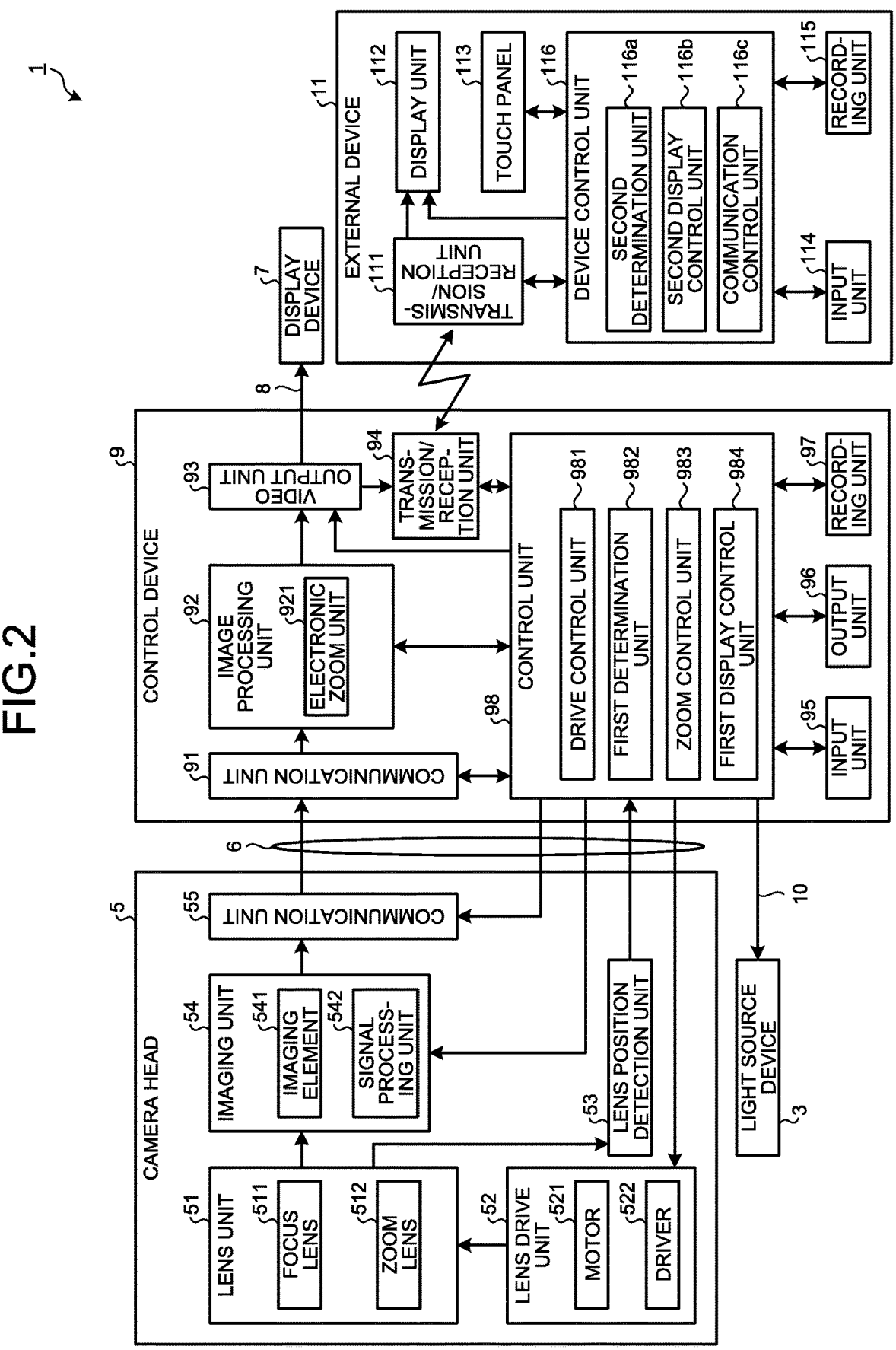
FIG. 2 is a block diagram illustrating functional configurations of a camera head, a control device, and an external device provided in the medical observation system according to the first embodiment.

Next, functional configurations of the camera head 5, the control device 9, and the external device 11 will be described. FIG. 2 is a block diagram illustrating the functional configurations of the camera head 5, the control device 9, and the external device 11 provided in the medical observation system 1. Incidentally, FIG. 2 does not illustrate the connectors CN1 and CN2 between the camera head 5 and control device 9, and the first transmission cable 6 and functional configurations of the light source device 3 and the display device 7 in order for convenience of the description.

[Configuration of Camera Head]

First, the functional configuration of the camera head 5 will be described.

The camera head 5 includes a lens unit 51, a lens drive unit 52, a lens position detection unit 53, an imaging unit 54, and a communication unit 55 as illustrated in FIG. 2.

The lens unit 51 is configured using a plurality of lenses movable along an optical axis, and forms the subject image condensed by the insertion section 2 on an imaging surface of the imaging unit 54 (an imaging element 541). The lens unit 51 includes: a focus lens 511 which is configured using one or a plurality of lenses and moves along the optical axis to adjust a focus; and a zoom lens 512 which is configured using one or a plurality of lenses and moves along the optical axis to change an angle of view. In addition, the lens unit 51 is also provided with a focus mechanism (not illustrated) which moves the focus lens 511 along the optical axis and a zoom mechanism (not illustrated) which moves the zoom lens 512 along the optical axis.

The lens drive unit 52 includes a motor 521 that operates the focus mechanism and the zoom mechanism of the lens unit 51 described above, and a driver 522 that drives the motor 521. The lens drive unit 52 adjusts the focus of the lens unit 51 or changes the angle of view under the control of the control device 9 to be described later.

The lens position detection unit 53 is configured using a position detection sensor such as a photo interrupter, and detects a lens position of the focus lens 511 on the optical axis and a lens position of the zoom lens 512 on the optical axis. The lens position detection unit 53 outputs detection results to the control device 9 via the first transmission cable 6.

The imaging unit 54 generates an image signal by receiving the subject image formed by the lens unit 51 and performing photoelectric conversion under the control of the control device 9 to be described later. The imaging unit 54 includes the imaging element 541 and a signal processing unit 542.

The imaging element 541 is configured using a charge coupled device (CCD), a complementary metal oxide semiconductor (CMOS) image sensor, or the like which optically receives a subject image condensed by the insertion section 2 and formed by the lens unit 51 and converts the received subject image into an electrical signal (analog signal). The effective number of pixels of the imaging element 541 is eight megapixels (for example, a so-called 4K resolution of 3840×2160 pixels) or more, and preferably 32 megapixels (for example, a so-called 8K resolution of 7680×4320 pixels) or more.

The signal processing unit 542 performs signal processing on an image signal (analog electrical signal) from the imaging element 541 and outputs a digital image signal (RAW signal (digital signal)). For example, for the image signal (analog electrical signal) from the imaging element 541, the signal processing unit 542 performs the signal processing, such as a process of removing reset noise, a process of multiplying an analog gain that amplifies the image signal, and A/D conversion.

The communication unit 55 functions as a transmitter that transmits the image signal (digital RAW signal) output from the imaging unit 54 to the control device 9 via the first transmission cable 6. The communication unit 55 is configured using a high-speed serial interface that performs communication of the image signal at a transmission rate of 1 Gbps or higher with the control device 9 via the first transmission cable 6, for example.

[Configuration of Control Device]

Next, the configuration of the control device 9 will be described.

As illustrated in FIG. 2, the control device 9 includes a communication unit 91, an image processing unit 92, and a video output unit 93, a transmission/reception unit 94, an input unit 95, an output unit 96, a recording unit 97, and a control unit 98.

The communication unit 91 functions as a receiver that receives an image signal (digital RAW signal) output from the camera head 5 (communication unit 55) via the first transmission cable 6. The communication unit 91 is configured using, for example, a high-speed serial interface that performs communication of the image signal at a transmission rate of 1 Gbps or higher with the communication unit 55.

Under control of the control unit 98, the image processing unit 92 performs predetermined image processing on the image signal, output from the camera head 5 and received by the communication unit 91, and outputs the image signal to the video output unit 93. Specifically, the image processing unit 92 multiplies the image signal by a digital gain that amplifies the signal. In addition, the image processing unit 92 performs RAW processing, such as optical black subtraction processing and demosaicing processing, on the image signal after being multiplied by the digital gain, and converts such a RAW signal (image signal) into an RGB signal (image signal). Further, the image processing unit 92 performs RGB processing, such as a white balance adjustment process of respectively multiplying RGB values by gains, RGB gamma correction, and YC conversion (converting the RGB signal into a luminance signal and a color difference signal (Y, $C_B/C_R$ signal)), on the RGB signal (image signal). In addition, the image processing unit 92 includes an electronic zoom unit 921.

The electronic zoom unit 921 generates an image signal of an enlarged image, generated by executing enlargement processing of enlarging a predetermined area by cutting out a predetermined area and performing resizing processing under the control of the control unit 98, and outputs the generated signal to the video output unit 93.

Under the control of the control unit 98, the video output unit 93 performs on-screen display (OSD) processing or the like to generate a display image (video signal) for display on which various types of information relating to the medical observation system 1 have been superimposed and outputs the generated image to the display device 7.

Under the control of the control unit 98, the transmission/reception unit 94 transmits the video signal and various types of information to the external device 11, and outputs various types of information received from the external device 11 to the control unit 98 according to a predetermined communication standard. Here, the predetermined communication standard is any communication scheme of wireless fidelity (Wi-Fi) (registered trademark) communication, Bluetooth (registered trademark) communication, communication using 5G wireless, 4G wireless, or 3G wireless, worldwide interoperability for microwave access (WiMAX) communication, and the like. It is a matter of course that other known communication standards can be applied as the communication standard.

The input unit 95 is configured using an operation device such as a mouse, a keyboard, and a touch panel, and receives a user operation performed by a user such as a doctor. Then, the input unit 95 outputs an operation signal corresponding to the user operation to the control unit 98.

The output unit 96 outputs various types of information under the control of the control unit 98. The output unit 96 is configured using a speaker, a display monitor, a printer, and the like.

The recording unit 97 records various programs to be executed by the medical observation system 1 and information that is being processed. The recording unit 97 is configured using a synchronous dynamic random access memory (SDRAM), a flash memory, or the like.

The control unit 98 integrally controls each unit of the medical observation system 1. The control unit 98 is configured using a CPU or the like. The control unit 98 includes a drive control unit 981, a first determination unit 982, a zoom control unit 983, and a first display control unit 984.

The drive control unit 981 controls each drive of the lens drive unit 52 and the imaging unit 54.

Specifically, the drive control unit 981 adjusts a focus position of the lens unit 51 by driving the lens drive unit 52 to move the focus lens 511 along the optical axis.

The first determination unit 982 determines whether an area, which includes a touch position and is cut out by the electronic zoom unit 921, is a predetermined resolution or higher. Here, the predetermined resolution is a resolution of two megapixels (a so-called 2K resolution of 1920×1080 pixels) or more, preferably eight megapixels (for example, a so-called 4K resolution of 3840×2160 pixels) or more.

When the first determination unit 982 determines that the area, which includes the touch position included in the instruction signal received from the external device 11, is not the predetermined resolution or higher, the zoom control unit 983 changes an area to be cut out by the electronic zoom unit 921 so as to include the touch position in the display image.

The first display control unit 984 controls the image processing unit 92 and the video output unit 93 to control a display mode of the display device 7. In addition, the first display control unit 984 causes the video output unit 93 to output the enlarged image generated by the electronic zoom unit 921 to the display device 7. Further, when the area to be cut out is changed by the zoom control unit 983, the first display control unit 984 causes the electronic zoom unit 921 to execute enlargement processing to generate an enlarged image by cutting out the changed area and performing resizing processing.

[Configuration of External Device]

Next, the configuration of the external device 11 will be described.

The external device 11 includes a transmission/reception unit 111, a display unit 112, a touch panel 113, an input unit 114, a recording unit 115, and a device control unit 116 as illustrated in FIG. 2.

Under the control of the device control unit 116, the transmission/reception unit 111 transmits various types of information to the control device 9 and outputs the various types of information received from the control device 9 to the device control unit 116 or the display unit 112 according to the same communication standard as the transmission/reception unit 94 of the control device 9.

The display unit 112 displays the various types of information received by the transmission/reception unit 111. Specifically, the display unit 112 displays a display image corresponding to the video signal received by the transmission/reception unit 111 from the control device 9. The display unit 112 is configured using liquid crystal, organic EL, or the like.

The touch panel 113 is provided so as to be superimposed on a display area of the display unit 112, detects a position of an external object coming in contact, and outputs a signal corresponding to the position to the device control unit 116. Specifically, the touch panel 113 detects a touch position of a user from the outside, and outputs a position signal (coordinate signal) according to the detected position to the device control unit 116. In addition, the touch panel 113 detects multi-touch operations such as a touch operation of causing a pointer, such as a user's finger and a stylus, to come in contact with the detection area of the touch panel 113, a tap operation of touching the touch panel 113 two or more times within a predetermined time, a long-press operation of pressing a touch position with a pointer for a predetermined time (for example, one second) or longer, a slide operation (swipe operation) or a flick operation of sliding a pointer in the state of coming in contact with the touch panel 113, a pinch-in operation of reducing a distance between pointers in a state where the pointers come in contact with two different positions in a detection area of touch panel 113 or a pinch-out operation of increasing the distance between the pointers in the state of coming in contact with the two points, and a rotation operation of setting one pointer as a rotation center and slidably rotating another pointer between the two pointers in the detection area of the touch panel 113. It is a matter of course that the touch panel 113 may detect a shape such as a circle, an ellipse, and a polygon, a figure, a character, or the like formed in accordance with a trajectory of a pointer on the detection area.

The input unit 114 receives inputs of various operations relating to the external device 11. The input unit 114 is configured using a switch, a button, and the like.

The recording unit 115 records various programs to be executed by the external device 11 and information that is being processed. The recording unit 115 is configured using an SDRAM, a flash memory, or the like.

The device control unit 116 integrally controls the respective units of the external device 11. The device control unit 116 is configured using a CPU or the like. The device control unit 116 includes a second determination unit 116a, a second display control unit 116b, and a communication control unit 116c.

The second determination unit 116a determines whether an area including a touch position is a predetermined resolution or higher. Here, the predetermined resolution is a resolution of two megapixels (a so-called 2K resolution of 1920×1080 pixels) or more, preferably eight megapixels (for example, a so-called 4K resolution of 3840×2160 pixels) or more.

The second display control unit 116b controls a display mode of the display unit 112. Specifically, a display image corresponding to the video signal received by the transmission/reception unit 111 is displayed on the display unit 112. In addition, the second display control unit 116b displays area information indicating an area, which includes a touch position of a user and satisfies a predetermined resolution, on the display unit 112 to be superimposed on the display image based on the instruction signal output from the touch panel 113. Further, when the second determination unit 116a determines that the area including the touch position is not the predetermined resolution or higher, the second display control unit 116b changes a superimposition position of the area information so as to include the touch position and displays the area information on the display unit 112.

The communication control unit 116c controls the transmission/reception unit 111. Specifically, the communication control unit 116c causes the transmission/reception unit 111 to transmit an instruction signal including the touch position at which the touch panel 113 has received an input to the control device 9.

[Processing of Medical Observation System]

Figure 3:
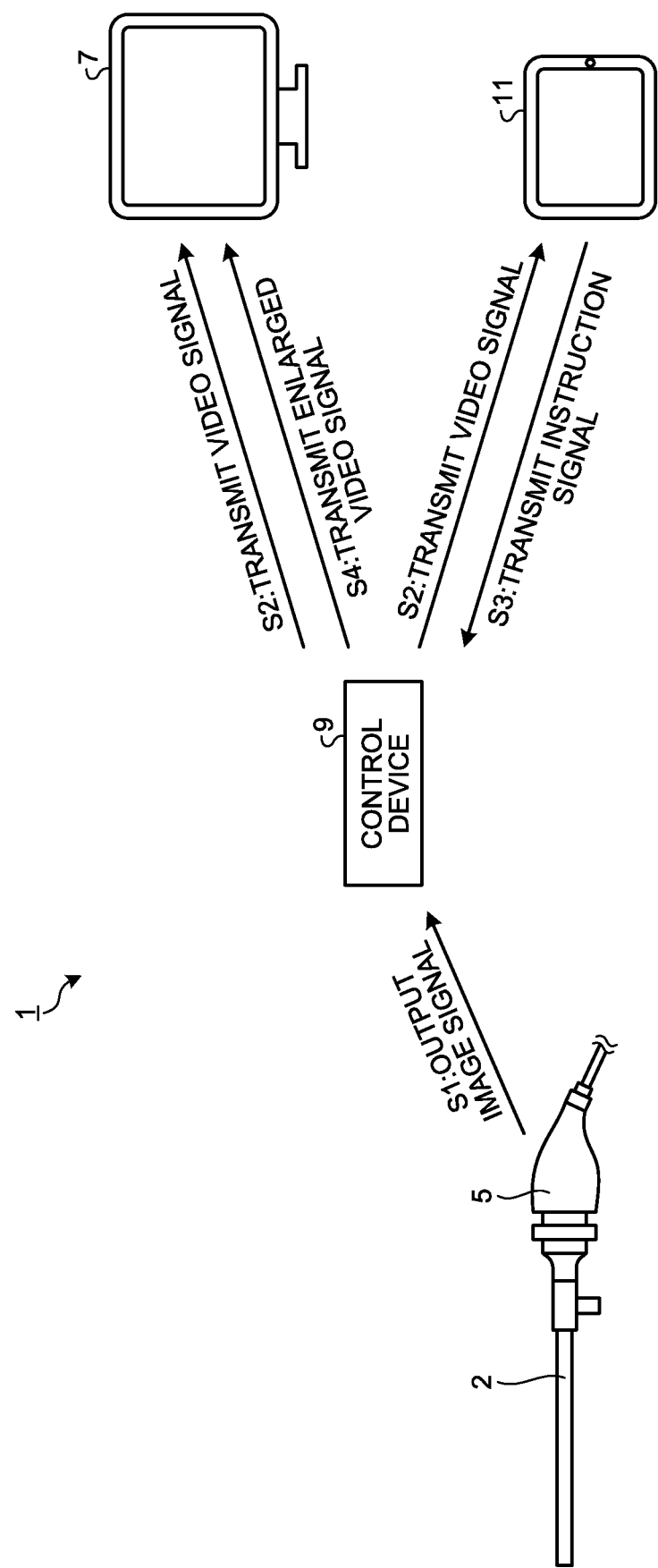
FIG. 3 is a diagram illustrating an outline of processing to be executed by the medical observation system according to the first embodiment.

Next, processing to be executed by the medical observation system 1 will be described. FIG. 3 is a diagram illustrating an outline of the processing to be executed by the medical observation system 1.

As illustrated in FIG. 3, first, the camera head 5 outputs an image signal captured through the insertion section 2 to the control device 9 (Step S1).

Figure 4:
FIG. 4 is a view illustrating an example of a display image displayed by a display device and the external device according to the first embodiment.

Subsequently, the control device 9 generates a video signal based on the image signal output from the camera head 5, and transmits the video signal to each of the display device 7 and the external device 11 (Step S2). Specifically, the control device 9 transmits a display image LV1 (live-view image) corresponding to a video signal illustrated in FIG. 4 to each of the display device 7 and the external device 11. As a result, the display device 7 and the external device 11 can display the display image LV1 at substantially the same timing.

Figure 5:
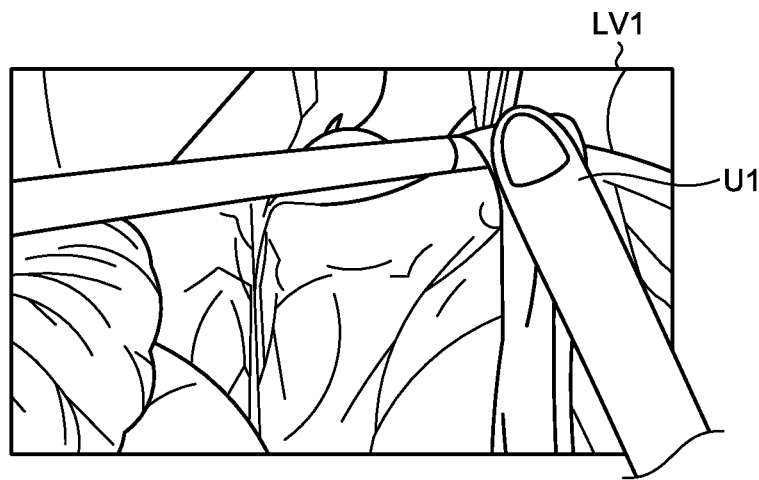
FIG. 5 is a view schematically illustrating an operation on a touch panel of the external device according to the first embodiment.

Thereafter, the external device 11 transmits an instruction signal corresponding to a position signal at which the touch panel 113 has received an input to the control device 9 (Step S3). Specifically, the external device 11 transmits the instruction signal giving an instruction on enlargement of an area including the touch position touched by a user U1 to the control device 9 via the touch panel 113 as illustrated in FIG. 5.

Figure 6:
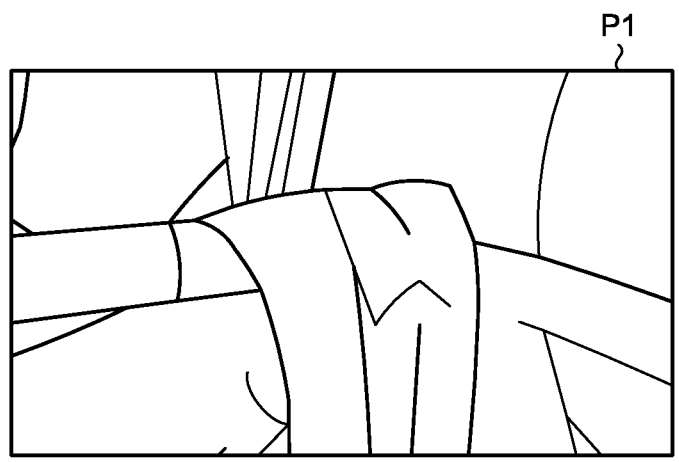
FIG. 6 is a view illustrating an example of an enlarged image displayed by the display device according to the first embodiment.

Then, the control device 9 transmits a video signal (enlarged image) obtained by enlarging the area including the touch position touched by the user U1 to the display device 7 based on the instruction signal from the external device 11 (Step S4). Specifically, the control device 9 transmits an enlarged image P1 corresponding to the video signal obtained by enlarging the area including the touch position touched by the user U1 to the display device 7 based on the instruction signal from the external device 11 as illustrated in FIG. 6. As a result, even under a situation where a hand of an operator such as a doctor and a scopist in a clean area is not available, predetermined processing, for example, enlargement processing can be performed on a position desired by the operator as a third party such as a nurse, an attending doctor, and an assistant in an unclean area operates the external device 11. Further, the operator can enlarge a desired area without moving the insertion section 2 to the vicinity where treatment using a treatment tool or the like is performed on a subject such as a patient, and thus, it is possible to not only mitigate adhesion of dirt or a living body to the insertion section 2 (endoscope) but also reduce steps for adjustment and movement of the position of the insertion section 2 (endoscope).

[Processing of Control Device]

Figure 7:
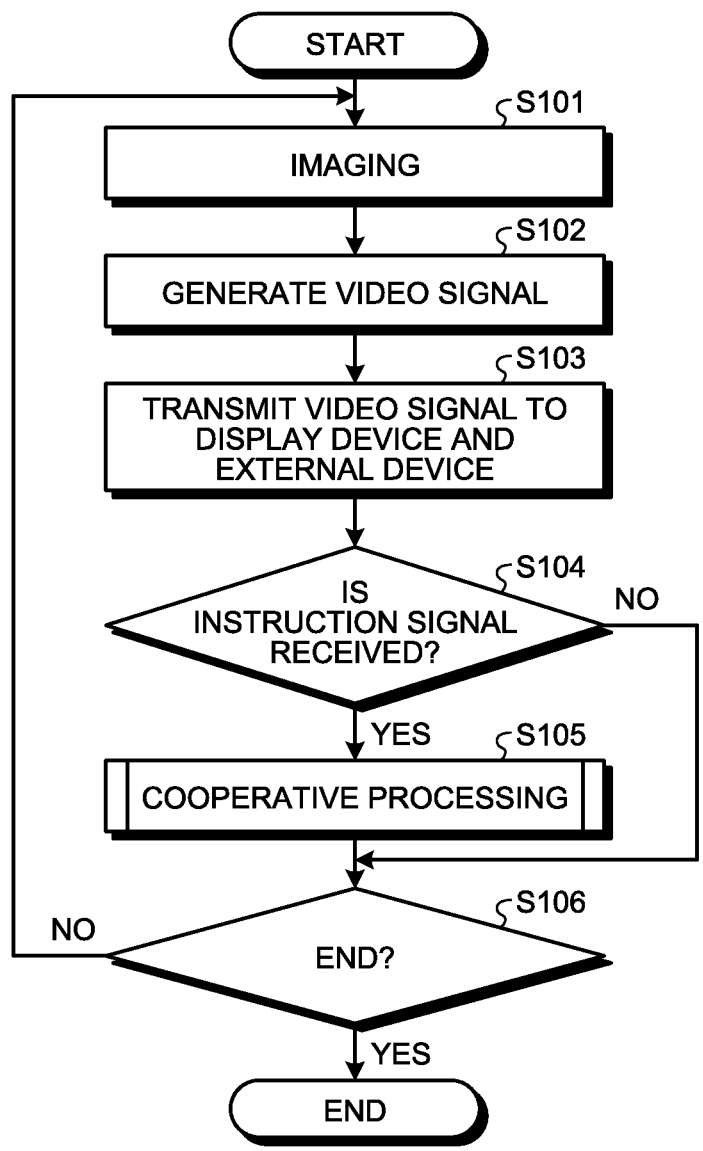
FIG. 7 is a flowchart illustrating an outline of processing to be executed by the control device according to the first embodiment.

Next, processing to be executed by the control device 9 performs will be described. FIG. 7 is a flowchart illustrating an outline of the processing to be executed by the control device 9.

As illustrated in FIG. 7, first, the drive control unit 981 causes the imaging unit 54 to perform imaging (Step S101), and causes the image processing unit 92 to generate a video image based on an image signal generated by the imaging unit 54 (Step S102).

Subsequently, the first display control unit 984 causes the video output unit 93 to transmit the video signal to the display device 7, and causes the transmission/reception unit 94 to transmit the video signal to the external device 11 (Step S103).

Thereafter, when the transmission/reception unit 94 receives an instruction signal from the external device 11 (Step S104: Yes), the control device 9 executes cooperative processing which executes predetermined processing in cooperation with each other according to the instruction signal transmitted from the external device 11 (Step S105). After Step S105, the control device 9 proceeds to Step S106 to be described later. Details of the cooperative processing will be described later. On the other hand, when the transmission/reception unit 94 has not received the instruction signal from the external device 11 (Step S104: No), the control device 9 proceeds to Step S106 to be described later.

Subsequently, when the input unit 95 receives an end input (Step S106: Yes), the control device 9 ends the present processing. On the other hand, when the input unit 95 has not received the end input (Step S106: No), the control device 9 returns to the above-described Step S101.

[Cooperative Processing]

Figure 8:
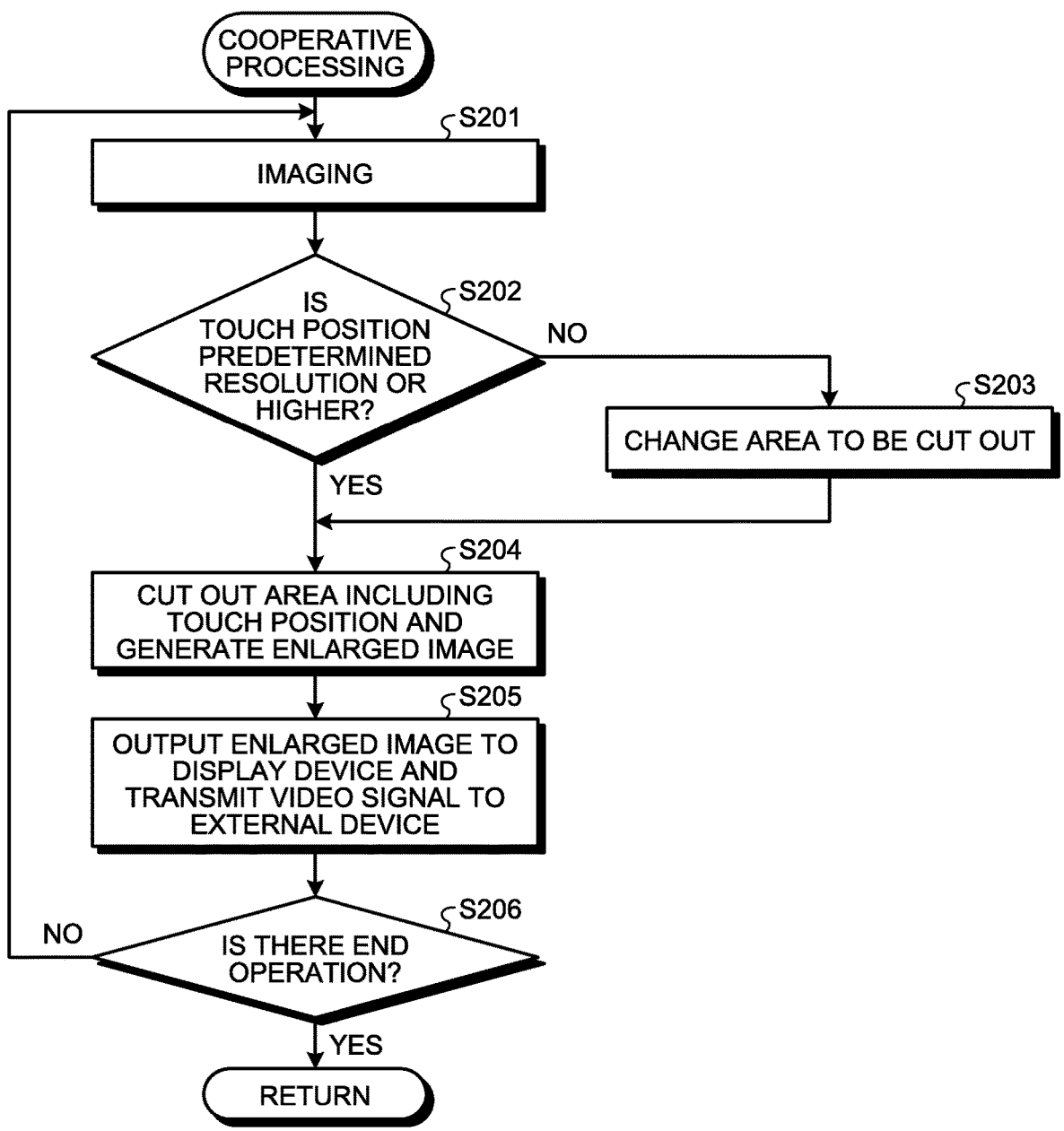
FIG. 8 is a flowchart illustrating an outline of cooperative processing of FIG. 7.

Next, the details of the cooperative processing described in Step S105 of FIG. 7 will be described. FIG. 8 is a flowchart illustrating an outline of the cooperative processing.

As illustrated in FIG. 8, first, the drive control unit 981 causes the imaging unit 54 to perform imaging (Step S201).

Subsequently, the first determination unit 982 determines whether an area, which includes a touch position and is cut out by the electronic zoom unit 921, is a predetermined resolution or higher (Step S202).

Figure 9A:
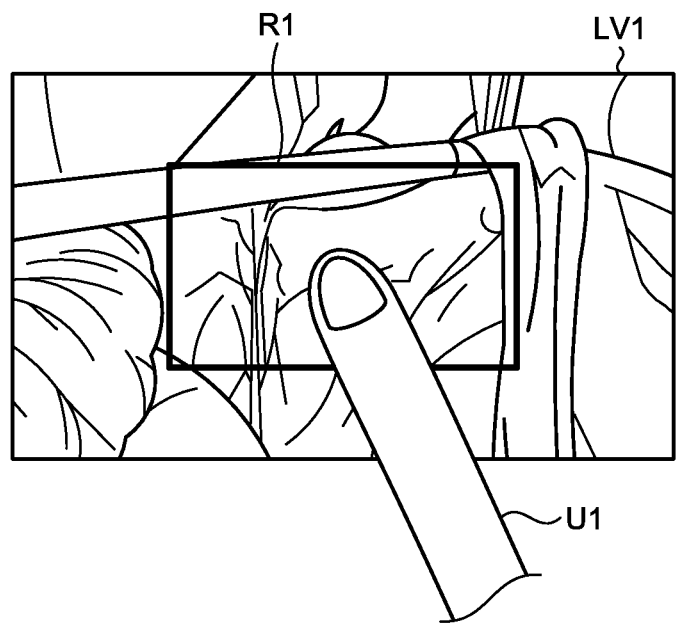
FIG. 9A is a view schematically describing a determination method by a first determination unit according to the first embodiment.

Specifically, the first determination unit 982 determines whether an area R1, which includes the touch position touched, via the touch panel 113, by the user U1 on the display image LV1 displayed by the display unit 112 of the external device 11, is the predetermined resolution or higher as illustrated in FIG. 9A. In this case, the first determination unit 982 determines whether an area centered on the touch position is the predetermined resolution or higher. When the first determination unit 982 determines that the area including the touch position cut out by the electronic zoom unit 921 is the predetermined resolution or higher (Step S202: Yes), the control device 9 proceeds to Step S204 to be described later.

Figure 9B:
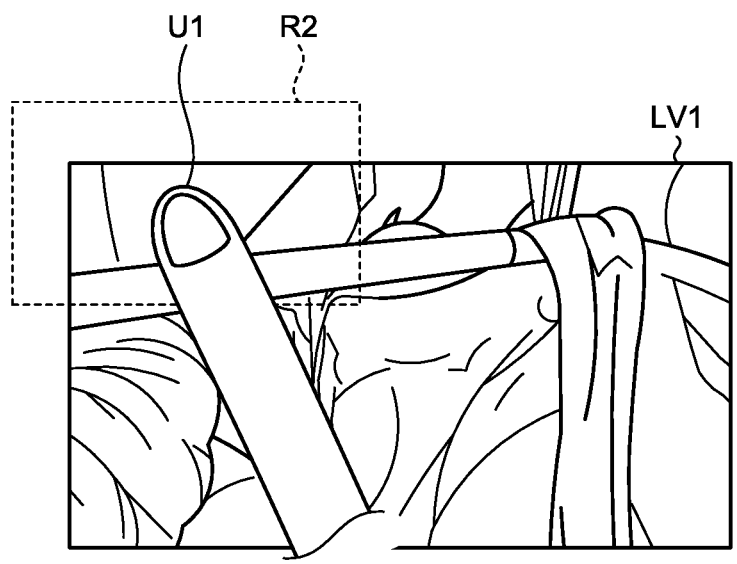
FIG. 9B is a view schematically describing the determination method by the first determination unit according to the first embodiment.

When the first determination unit 982 determines in Step S202 that the area including the touch position cut out by the electronic zoom unit 921 is not the predetermined resolution or higher (Step S202: No), the control device 9 proceeds to Step S203 to be described later. Specifically, when the area R1, which includes the touch position touched, via the touch panel 113, by the user U1 on the display image LV1 displayed by the display unit 112 of the external device 11, is not the predetermined resolution or higher, for example, when the user U1 touches a corner of the display image LV1 and an area R2 including such a touch position is lower than the predetermined resolution as illustrated in FIG. 9B, the first determination unit 982 determines that the area including the touch position cut out by the electronic zoom unit 921 is not the predetermined resolution or higher.

Figure 9C:
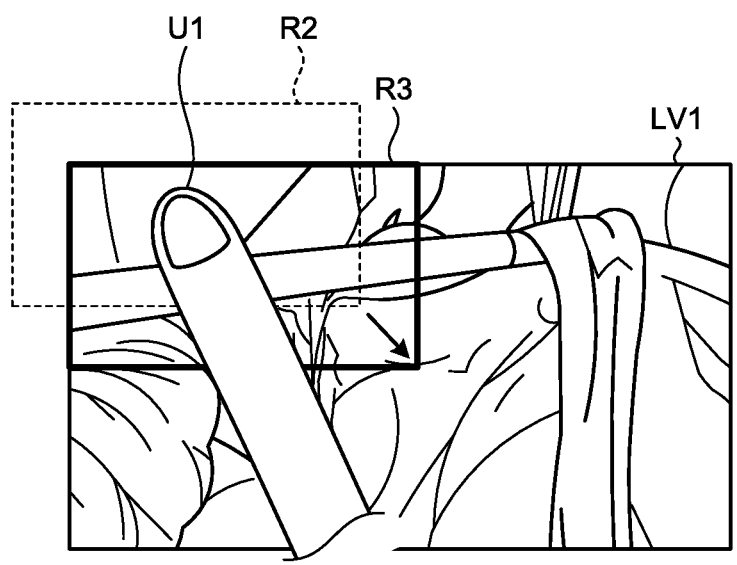
FIG. 9C is a view schematically describing a change of an area by a zoom control unit according to the first embodiment.

Subsequently, the zoom control unit 983 changes an area to be cut out by the electronic zoom unit 921 (Step S203). Specifically, the zoom control unit 983 changes the area to be cut out by the electronic zoom unit 921 to an area R3 having a predetermined resolution or higher as illustrated in FIG. 9C. Thus, even when the user U1 touches the corner of the display image LV1 or a position lower than the predetermined resolution, it is possible to maintain the image quality of the display image to be displayed by the display device 7. After Step S203, the control device 9 proceeds to Step S204.

Subsequently, the first display control unit 984 causes the electronic zoom unit 921 to cut out an area including a position according to the instruction signal from the display image and execute enlargement processing to generate an enlarged image (Step S204). Specifically, the first display control unit 984 causes the electronic zoom unit 921 to execute the enlargement processing to cut out and enlarge a predetermined area including the position corresponding to the instruction signal, thereby generating a video signal of the enlarged image obtained by enlarging the area including the touch position.

Thereafter, the first display control unit 984 causes the video output unit 93 to transmit the enlarged image (an enlarged video signal, for example, the above-described enlarged image P1 of FIG. 6) generated by the electronic zoom unit 921 to the display device 7, and causes the transmission/reception unit 94 to transmit the video signal (the display image LV1 of FIG. 4) to the external device 11 (Step S205). As a result, the display device 7 displays the above-described enlarged image P1 of FIG. 6, and the external device 11 displays the display image LV1 of FIG. 4, and thus, the operator can perform treatment on a subject while confirming the enlarged image obtained by enlarging a desired position without adjusting an imaging direction of the insertion section 2.

Subsequently, when an input of an end operation is received from the input unit 95 or the external device 11 (Step S206: Yes), the control device 9 returns to the main routine of FIG. 7. Specifically, here, the end operation corresponds to, for example, a case where the touch panel 113 detects a new touch position from the external device 11 and receives an instruction signal, a case where the input unit 95 or the input unit 114 receives an input of an instruction signal to end the enlarged image, a case where an instruction signal to give an instruction on reduction of the enlarged image is received from the external device 11, and the like.

In Step S204, when the input unit 114 or the touch panel 113 has not received the input of the end operation (Step S206: No), the control device 9 returns to Step S201.

[Processing of External Device]

Figure 10:
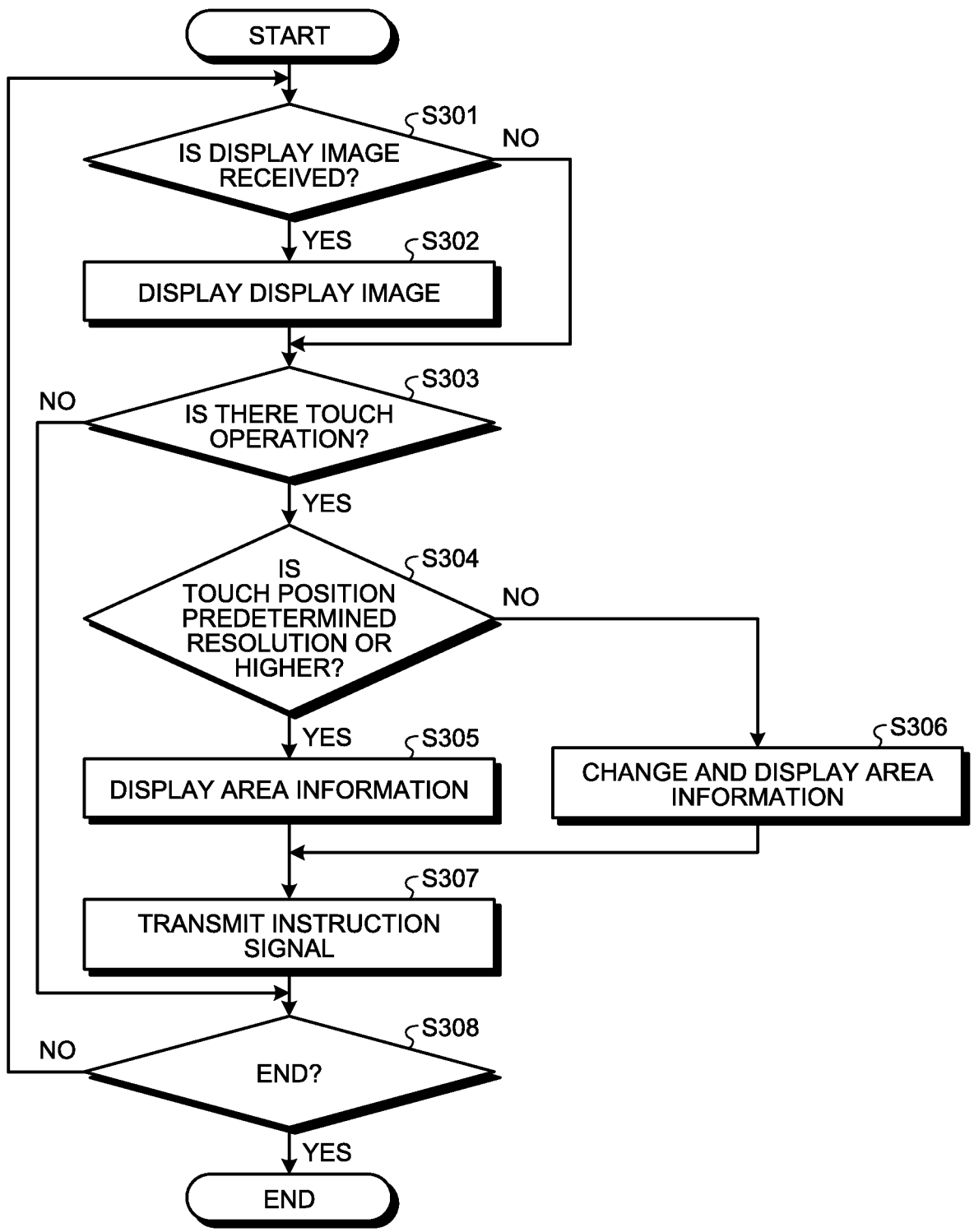
FIG. 10 is a flowchart illustrating an outline of processing to be executed by the external device according to the first embodiment.

Next, processing to be executed by the external device 11 will be described. FIG. 10 is a flowchart illustrating an outline of the processing to be executed by the external device 11.

As illustrated in FIG. 10, when the transmission/reception unit 111 receives a display image (video signal) from the control device 9 (Step S301: Yes), the second display control unit 116b causes the display unit 112 to display the display image corresponding to the video signal received from the control device 9 (Step S302).

Figure 11A:
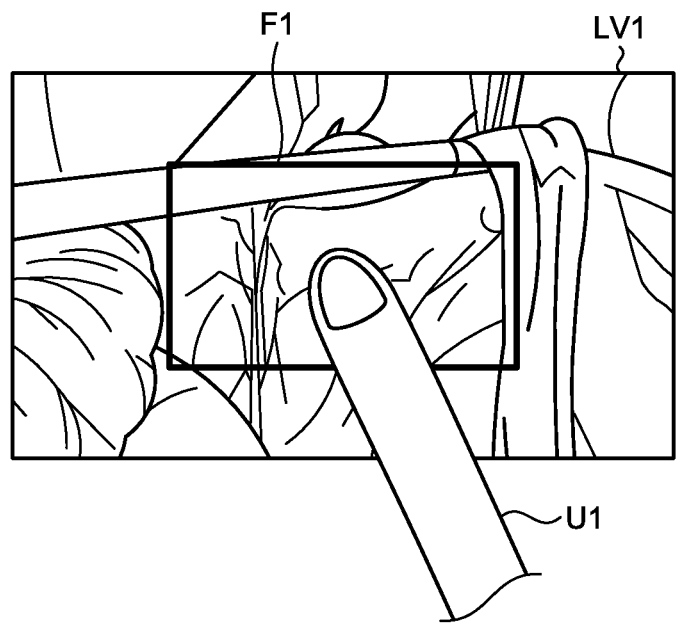
FIG. 11A is a view schematically illustrating an example of an image displayed by a display unit of the external device according to the first embodiment.

Subsequently, when there is a touch operation on the touch panel 113 (Step S303: Yes), the second determination unit 116a determines whether an area including a touch position is a predetermined resolution or higher (Step S304). Specifically, the second determination unit 116a performs the same determination as the first determination unit 982 in FIG. 8 described above. When the second determination unit 116*a* determines that the area including the touch position is the predetermined resolution or higher (Step S304: Yes), the second display control unit 116*b* displays area information, which indicates the area including the touch position and satisfying the predetermined resolution, on the display unit 112 to be superimposed on the display image LV1 (Step S305). Specifically, the second display control unit 116*b* displays area information F1, which indicates the area including the touch position and satisfying the predetermined resolution, on the display unit 112 to be superimposed on the display image LV1 as illustrated in FIG. 11A. As a result, the user U1 of the external device 11 can intuitively grasp a cutout area when electronic zooming is performed by the control device 9. After Step S305, the external device 11 proceeds to Step S307 to be described later.

Figure 11B:
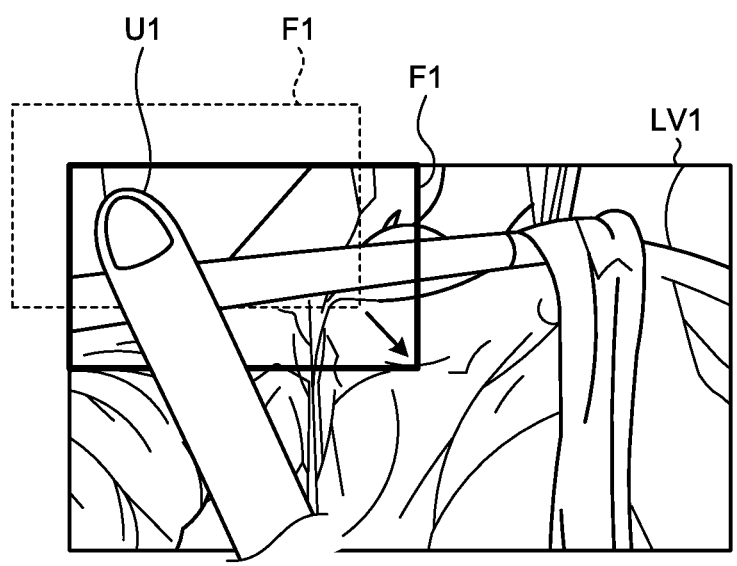
FIG. 11B is a view schematically illustrating the example of the image displayed by the display unit of the external device according to the first embodiment.

When the second determination unit 116*a* determines in Step S304 that the area including the touch position is not the predetermined resolution or higher (Step S304: No), the second display control unit 116*b* changes area information, which indicates the area including the touch position and satisfying the predetermined resolution, and displays the changed area information on the display unit 112 to be superimposed on the display image LV1 (Step S306). Specifically, the second display control unit 116*b* changes (moves) a display position of the area information F1 indicating the area including the touch position and satisfying the predetermined resolution to a position satisfying the predetermined resolution on the display image LV1, and displays the area information F1 on the display unit 112 to be superimposed on the display image LV1 as illustrated in FIG. 11B. As a result, the user U1 of the external device 11 can intuitively grasp the cutout area when the electronic zooming is performed by the control device 9, and it is possible to prevent an erroneous operation since the cutout area by the electronic zooming is emphasized and displayed even when the user U1 has touched a corner of the display image LV1 or a position lower than the predetermined resolution.

Subsequently, the communication control unit 116*c* transmits an instruction signal including the touch position at which the touch panel 113 has received an input to the control device 9 (Step S307).

Thereafter, when the input unit 114 or the touch panel 113 receives the input of the instruction signal to give an instruction on end (Step S308: Yes), the external device 11 ends the process. On the other hand, when the input unit 114 or the touch panel 113 has not received the input of the instruction signal to give the instruction on the end (Step S308: No), the external device 11 returns to Step S301 described above.

In Step S301, when the transmission/reception unit 111 has not received the video signal from the control device 9 (Step S301: No), the external device 11 proceeds to Step S303.

In Step S303, when there is no touch operation on the touch panel 113 (Step S303: No), the external device 11 proceeds to Step S308.

According to the first embodiment described above, the first display control unit 984 causes the electronic zoom unit 921 to execute the enlargement processing to cut out and enlarge the area including the position according to the instruction signal from the display image and generate the enlarged image, and causes the video output unit 93 to output the enlarged image (enlarged video signal) to the display device 7. Thus, it is possible to easily enlarge and display a desired area of interest during treatment even under a situation where the operator's hand is not available.

In addition, according to the first embodiment, the zoom control unit 983 changes the area to be cut out by the electronic zoom unit 921 so as to include the touch position in the display image when the first determination unit 982 determines that the area, which includes the touch position included in the instruction signal input from the external device 11, is not the predetermined resolution or higher. Thus, the display device 7 can display the enlarged image satisfying the resolution of the display device 7.

Figure 12A:
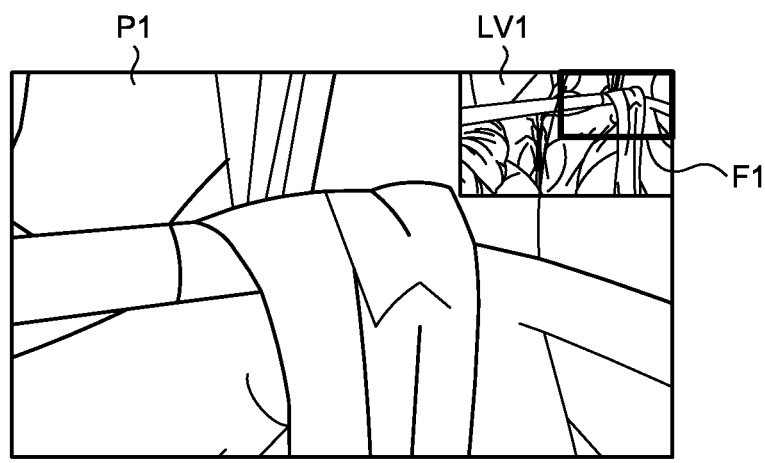
FIG. 12A is a view illustrating an example of another image displayed by the external device according to the first embodiment.
Figure 12B:
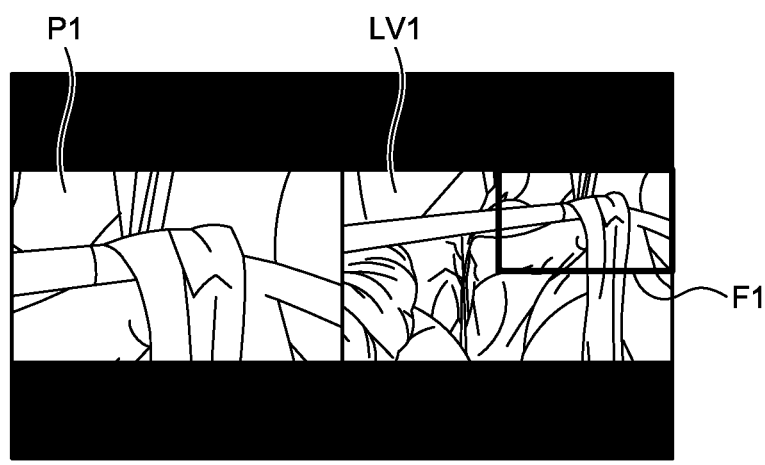
FIG. 12B is a view illustrating the example of the other image displayed by the external device according to the first embodiment.

Incidentally, the first display control unit 984 causes the display device 7 to display the enlarged image P1 when there is the instruction signal from the external device 11 in the first embodiment, but the invention is not limited thereto, and the display device 7 can perform display in various display modes. For example, the first display control unit 984 may cause the video output unit 93 to superimpose the display image LV1 of the entire image on the enlarged image P1 and transmit the superimposed display image LV1 to the display device 7 as illustrated in FIG. 12A. As a result, the operator can perform treatment while viewing the display image LV1 in a bird's eye view while viewing the current enlarged image P1. It is a matter of course that the first display control unit 984 may cause the video output unit 93 to transmit the enlarged image P1 and the display image LV1 of the entire image in parallel to the display device 7 as illustrated in FIG. 12B.

Figure 13A:
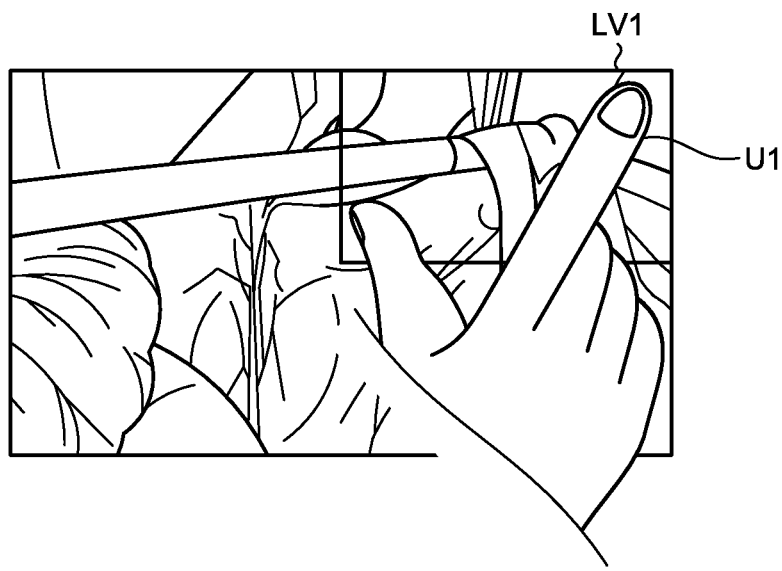
FIG. 13A is a view illustrating an example of an image displayed by the external device according to the first embodiment.
Figure 13B:
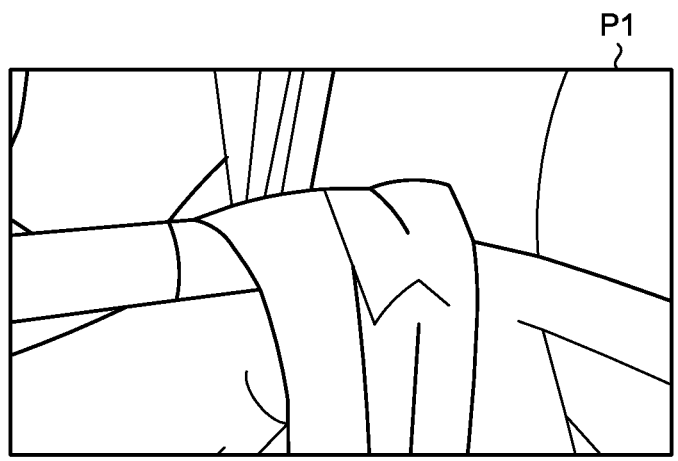
FIG. 13B is a view illustrating the example of the image displayed by the display device according to the first embodiment.

In addition, the area including the touch position touched by the touch panel 113 is enlarged in the first embodiment, but the invention is not limited thereto, and electronic zooming may be performed to enlarge or reduce an area determined according to a pinch-out operation or a pinch-in operation on the touch panel 113. For example, as illustrated in FIG. 13A, when the user U1 of the external device 11 has touched the touch panel 113 at two positions different from each other, the communication control unit 116*c* causes the transmission/reception unit 111 to transmit an instruction signal including the two different touch positions. As a result, the zoom control unit 983 sets a size of an area to be cut out by the electronic zoom unit 921 according to a distance between the two different touch positions as illustrated in FIG. 13B. Then, the first display control unit 984 causes the electronic zoom unit 921 to execute enlargement processing to cut out and enlarge the area set by the zoom control unit 983 and generate the enlarged image P1. It is a matter of course that the zoom control unit 983 may change a size of an area to be cut out by the electronic zoom unit 921 according to a distance between the two different touch positions. In this case, the first determination unit 982 may determine whether the area cut out by the electronic zoom unit 921 is the predetermined resolution or higher, and the zoom control unit 983 may set a size of an area to be cut out by the electronic zoom unit 921 based on the determination result of the first determination unit 982 and the distance between the two different touch positions.

In addition, the first display control unit 984 causes the video output unit 93 to output the video signals of the same resolution to the display device 7 and the external device 11, respectively, in the first embodiment, but the present invention is limited thereto, and the video output unit 93 may output video signals with different resolutions to the display device 7 and the external device 11, respectively. For example, when the imaging element 541 has 32 megapixels (a so-called 8K resolution) or more, the first display control unit 984 may cause the video output unit 93 to output a video signal of eight megapixels (a so-called 4K resolution) to the display device 7 and output a video signal of 32 megapixels (a so-called 8K resolution) to the external device 11. In this case, the second display control unit 116*b* of the external device 11 may cause the display unit 112 to display a frame corresponding to an area of a display image displayed by the display device 7 in a superimposed manner. As a result, the user of the external device 11 can intuitively grasp the area of the display image displayed on the display device 7, and send an advice to the operator while confirming an area of interest outside an imaging field of view during surgery. It is a matter of course that, when the imaging element 541 has 32 megapixels (a so-called 8K resolution) or more, the first display control unit 984 may cause the video output unit 93 to output a video signal of 32 megapixels (a so-called 8K resolution) to the display device 7 and output a video signal of eight megapixels (a so-called 4K resolution) to the external device 11, and may change the number of pixels of a video signal to be output to the display device 7 and the external device 11 as appropriate according to an operation received by the input unit 95.

Figure 14A:
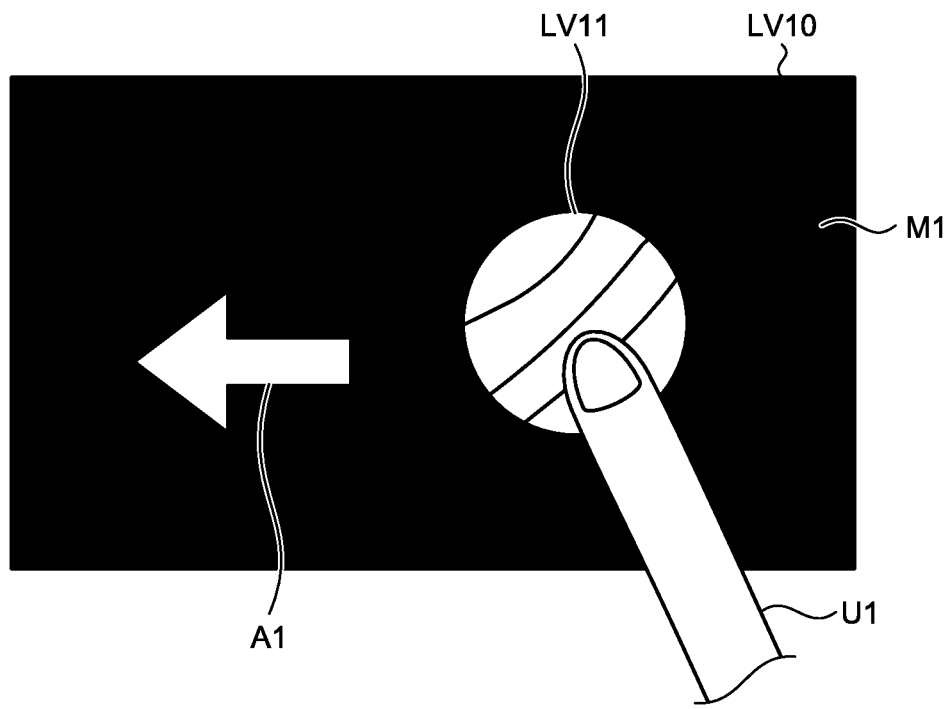
FIG. 14A is a view illustrating an example of another image displayed by the external device according to the first embodiment.
Figure 14B:
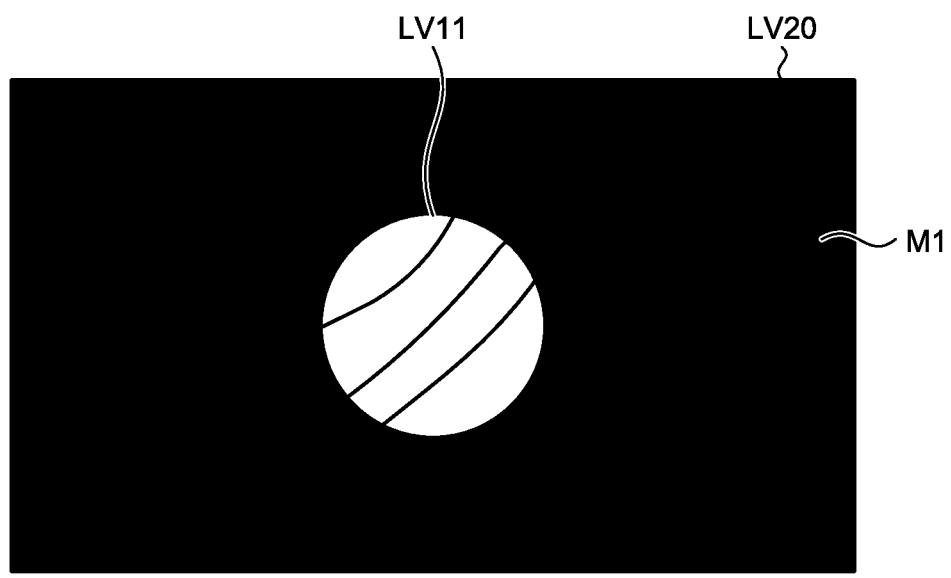
FIG. 14B is a view illustrating the example of the other image displayed by the display device according to the first embodiment.
Figure 14C:
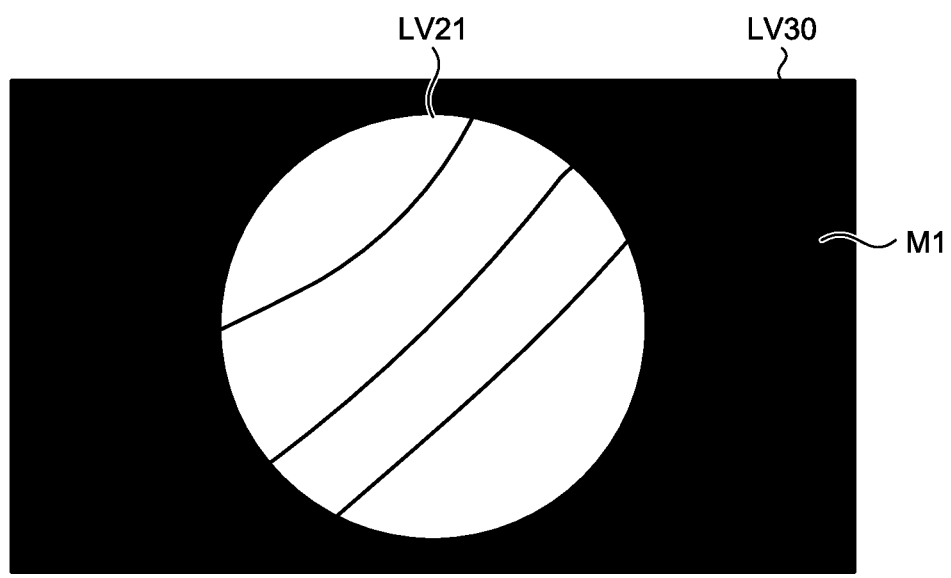
FIG. 14C is a view illustrating the example of the other image displayed by the display device according to the first embodiment.

In addition, the enlarged image is displayed on the display device 7 according to the instruction signal from the external device 11 in the first embodiment, but a display position of an effective image reflected in the display image may be changed, for example. Specifically, when there is a slide operation (an arrow A1) of touching an effective image LV11 (subject image) of a display image LV10 and moving the touched image the right side is performed on the touch panel 113 in a case where the display unit 112 of the external device 11 displays the display image LV10 as illustrated in FIG. 14A, the communication control unit 116*c* causes the transmission/reception unit 111 to transmit, to the control device 9, an instruction signal including a touch position and trajectory information of the touch position moving with a lapse of time. In this case, the first display control unit 984 of the control device 9 causes the video output unit 93 to transmit the display image LV20 in which the effective image LV11 has moved to the center to the display device 7 as illustrated in FIG. 14B. As a result, the effective image LV11 can be displayed at the center of the display device 7 even when an image eccentricity contact failure occurs due to a loose connection between the insertion section 2 and the camera head 5 and a display position of the effective image LV11 is shifted by a mask M1 (mask area). Further, as illustrated in FIG. 14C, the first display control unit 984 of the control device 9 may cause the electronic zoom unit 921 to generate an effective image LV21 (subject image) obtained by enlarging the effective image LV11 and cause the video output unit 93 to transmit a display image LV30 in which the effective image LV21 has been moved to the center to the display device 7. As a result, the effective image LV21 can be displayed at the center of the display device 7 even when the image eccentricity occurs due to the loose connection between the insertion section 2 and the camera head 5. Further, since the effective image LV21 is enlarged and displayed on the display device 7, it is possible to prevent shortage of the mask M1 (mask area).

In addition, the zoom control unit 983 changes the area to be cut out by the electronic zoom unit 921 so as to include the touch position in the display image when the first determination unit 982 determines that the area, which includes the touch position included in the instruction signal input from the external device 11, is not the predetermined resolution or higher in the first embodiment, but the invention is not limited thereto, and various changes may be made. For example, the zoom control unit 983 may change and set an area including the touch position and the center of the display image to an area to be cut out by the electronic zoom unit 921 when the first determination unit 982 determines that the area including the touch position included in the instruction signal input from the external device 11 is not the predetermined resolution or higher. It is a matter of course that the zoom control unit 983 may detect an area partially including a distal end of a treatment tool using template matching or the like in a known technique on the display image and change and set an area including such a detected area and the touch position to an area to be cut out by the electronic zoom unit 921.

Second Embodiment

Next, a second embodiment will be described. The second embodiment has the same configuration as the medical observation system 1 according to the first embodiment described above, and is different from the first embodiment in terms of overall processing to be executed by a medical observation system and cooperative processing to be executed by a control device. Specifically, the enlarged image obtained by enlarging the area including the touch position touched by the external device 11 is displayed on the display device 7 in the first embodiment described above, but control is performed to set a focus of the focus lens 511 on a touch position touched by the external device 11 in the second embodiment. Hereinafter, the entire processing to be executed by the medical observation system according to the second embodiment and the cooperative processing to be executed by the control device will be described. Incidentally, the same configurations with those of the medical observation system 1 according to the first embodiment described above will be denoted by the same reference signs, and descriptions thereof will be omitted.

[Processing of Medical Observation System]

FIG. 15 is a diagram illustrating an outline of processing to be executed by the medical observation system 1 according to the second embodiment. In FIG. 15, Steps S10 and S11 correspond to Steps S1 and S2 of FIG. 3 described above, respectively.

In Step S12, the external device 11 transmits, to the control device 9, an instruction signal to set a focus on a position where the touch panel 113 has received an input.

Subsequently, the control device 9 drives the focus lens 511 such that the focus lens 511 of the camera head 5 is focused at a position corresponding to an instruction signal received from the external device 11 where the touch panel 113 has received an input (Step S13). As a result, the control device 9 can generate a display image in which the focus is set to the position touched by a user of the external device 11.

[Cooperative Processing]

Figure 16:
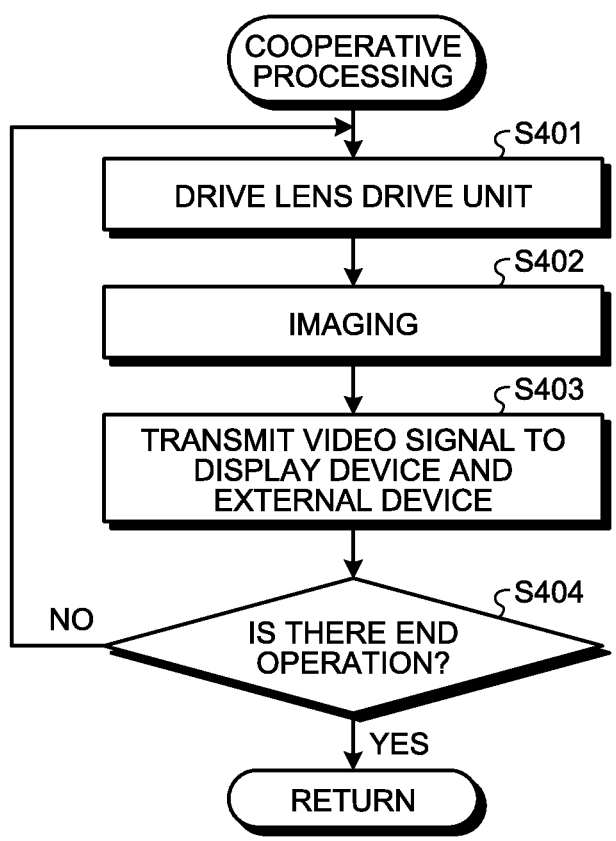
FIG. 16 is a flowchart illustrating an outline of cooperative processing to be executed by a control device according to the second embodiment.

Next, the cooperative processing to be executed by the control device 9 will be described. FIG. 16 is a flowchart illustrating an outline of the cooperative processing to be executed by the control device 9.

As illustrated in FIG. 16, first, the drive control unit 981 drives the lens drive unit 52 such that the focus lens 511 is focused at a position corresponding to an instruction signal received by the transmission/reception unit 94 (Step S401). As a result, it is possible to set the focus at the position touched by the user of the external device 11.

Subsequently, the drive control unit 981 causes the imaging unit 54 to image a subject image formed by the lens unit 51 (Step S402).

Thereafter, the first display control unit 984 causes the video output unit 93 to transmit a video signal to the display device 7, and causes the transmission/reception unit 94 to transmit the video signal to the external device 11 (Step S403). Step S404 corresponds to Step S206 of FIG. 8 described above. After Step S404, the control device 9 returns to the main routine of FIG. 7 described above.

According to the second embodiment described above, the drive control unit 981 drives the lens drive unit 52 such that the focus lens 511 is focused at the position corresponding to the instruction signal received by the transmission/reception unit 94, and thus, an operator can set the focus at a desired position even under a situation where the operator's hand is not available.

Incidentally, the lens unit 51 is focused at the position corresponding to the instruction signal received from the external device 11 in the second embodiment, but the invention is not limited thereto. For example, the control device 9 may change an image processing parameter (for example, a contrast, a saturation, a color, structure enhancement, or the like) of the image processing unit 92, brightness of illumination light to be emitted by the light source device 3, and a photometric area based on the position corresponding to the instruction signal received from the external device 11.

In addition, predetermined information, for example, a figure, a character, a mark, a symbol, and the like, may be superimposed at the position corresponding to the instruction signal received by the first display control unit 984 from the external device 11 in the second embodiment. Specifically, patient information, for example, a name, a gender, a medical condition, and an age, may be superimposed on the position corresponding to the instruction signal received by the first display control unit 984 from the external device 11.

In addition, the lens unit 51 may be focused at the position corresponding to the instruction signal received from the external device 11, and a video signal in which an area including a position corresponding to the instruction signal from the electronic zoom unit 921 of the first embodiment described above is enlarged may be transmitted to the display device 7 in the second embodiment. As a result, it is possible to display an enlarged image which has been in focus by a single operation on the display device 7.

Third Embodiment

Next, a third embodiment will be described. The third embodiment has a different configuration of the insertion section 2 of the medical observation system 1 according to the first embodiment described above, and is different from the first embodiment in terms of overall processing to be executed by a medical observation system and cooperative processing to be executed by a control device. Hereinafter, a configuration of the medical observation system according to the third embodiment will be described, and then, the overall processing to be executed by the medical observation system performs and the cooperative processing to be executed by the control device will be described in this order. Incidentally, the same configurations with those of the medical observation system 1 according to the first embodiment described above will be denoted by the same reference signs, and descriptions thereof will be omitted.

[Schematic Configuration of Medical Observation System]

Figure 17:
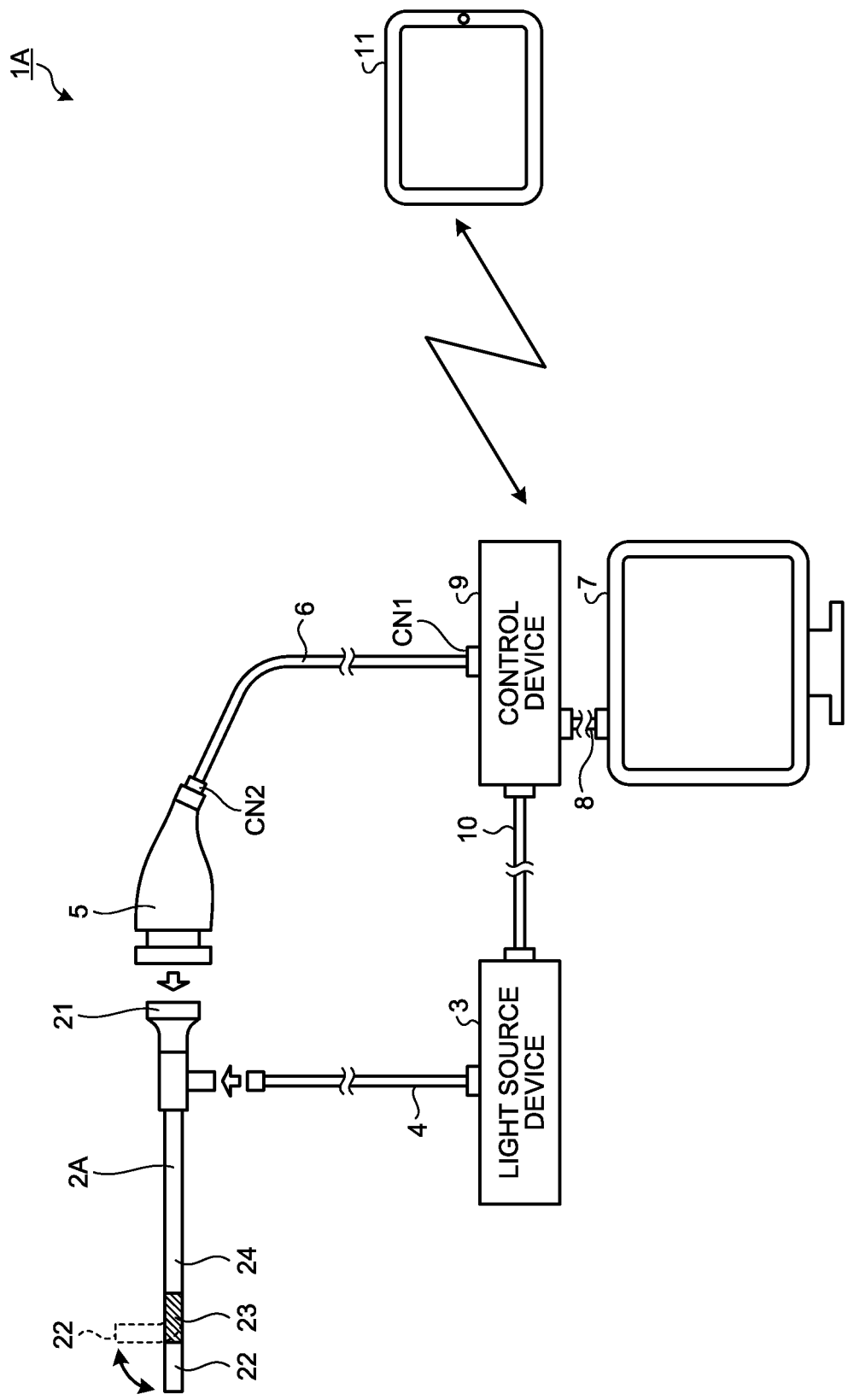
FIG. 17 is a diagram illustrating a schematic configuration of a medical observation system according to a third embodiment.

FIG. 17 is a diagram illustrating a schematic configuration of the medical observation system according to the third embodiment. A medical observation system 1A illustrated in FIG. 17 includes an insertion section 2A instead of the insertion section 2 (endoscope) of the medical observation system 1 according to the first embodiment described above.

The insertion section 2A is rigid or at least partially flexible and has an elongated shape, and is inserted into a subject such as a patient. In addition, the insertion section 2A includes a bending unit 23 which bends a distal end portion 22 in a predetermined direction under control of the control device 9. In addition, the insertion section 2A is provided with an optical system, which is configured using one or a plurality of lenses and forms an observation image, inside the insertion section 2.

Figure 18:
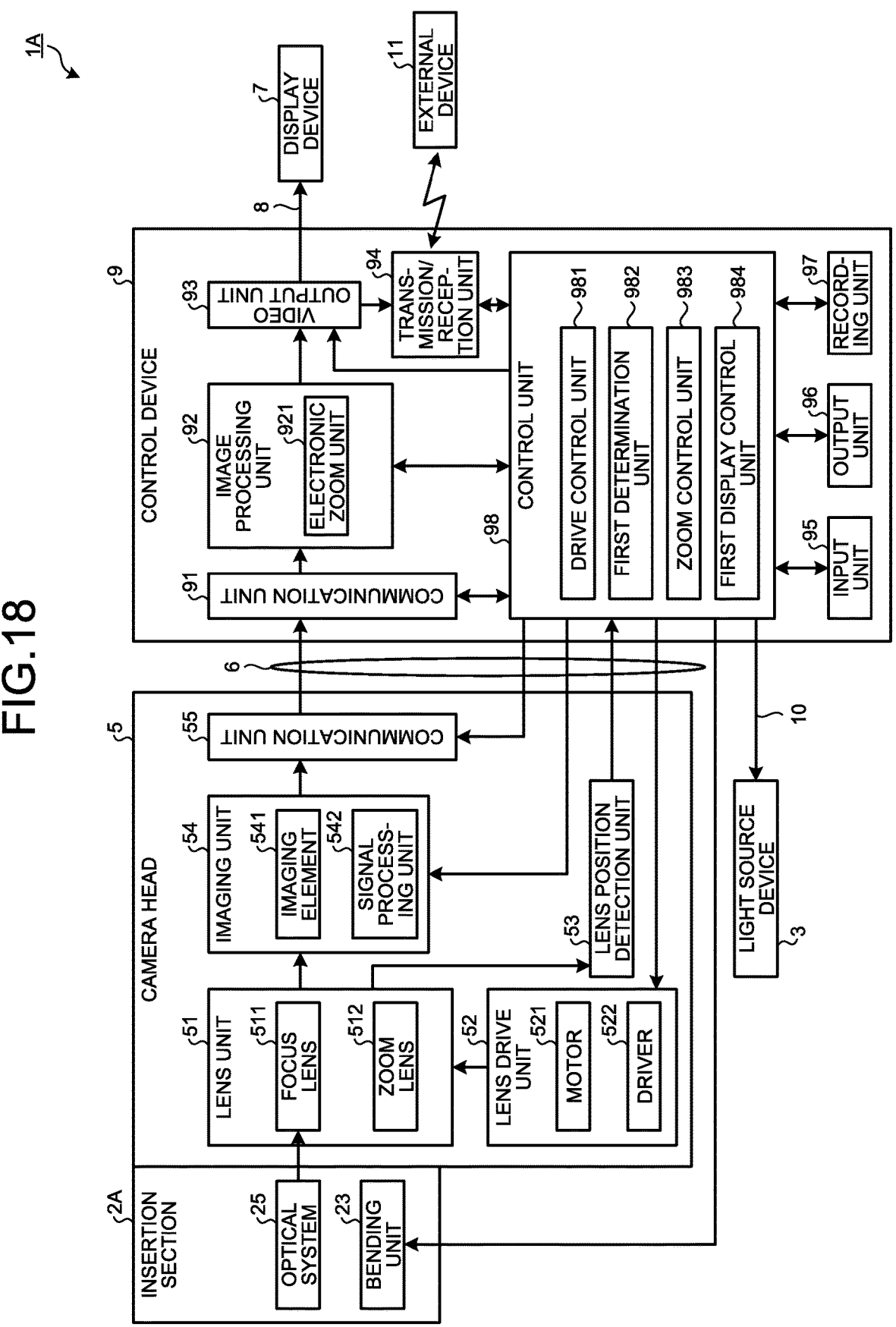
FIG. 18 is a block diagram illustrating functional configurations of an insertion section, a camera head, and a control device provided in the medical observation system according to the third embodiment.

Next, functional configurations of the insertion section 2A, the camera head 5, and the control device 9 will be described. FIG. 18 is a block diagram illustrating the functional configurations of the insertion section 2A, the camera head 5, and the control device 9 provided in the medical observation system 1A. Incidentally, FIG. 18 does not illustrate the connectors CN1 and CN2 between the camera head 5 and control device 9, and the first transmission cable 6 and functional configurations of the light source device 3, the display device 7, and the external device 11 in order for convenience of the description.

[Configuration of Insertion Section]

The functional configuration of the insertion section 2A will be described.

The insertion section 2A includes at least the bending unit 23 and an optical system 25 as illustrated in FIG. 18.

The bending unit 23 is configured using a plurality of bending pieces, and bends in vertical and horizontal directions. One end of the bending unit 23 is connected with the distal end portion 22 (see FIG. 16) and the other end thereof is connected with a body section 24 (see FIG. 16). The bending unit 23 bends the distal end portion 22 in the vertical and horizontal directions under the control of the control device 9.

The optical system 25 is configured using one or a plurality of lenses, and forms a subject image (observation image) on a light receiving surface of the imaging element 541 of the camera head 5 via the lens unit 51 of the camera head 5.

[Processing of Medical Observation System]

Figure 19:
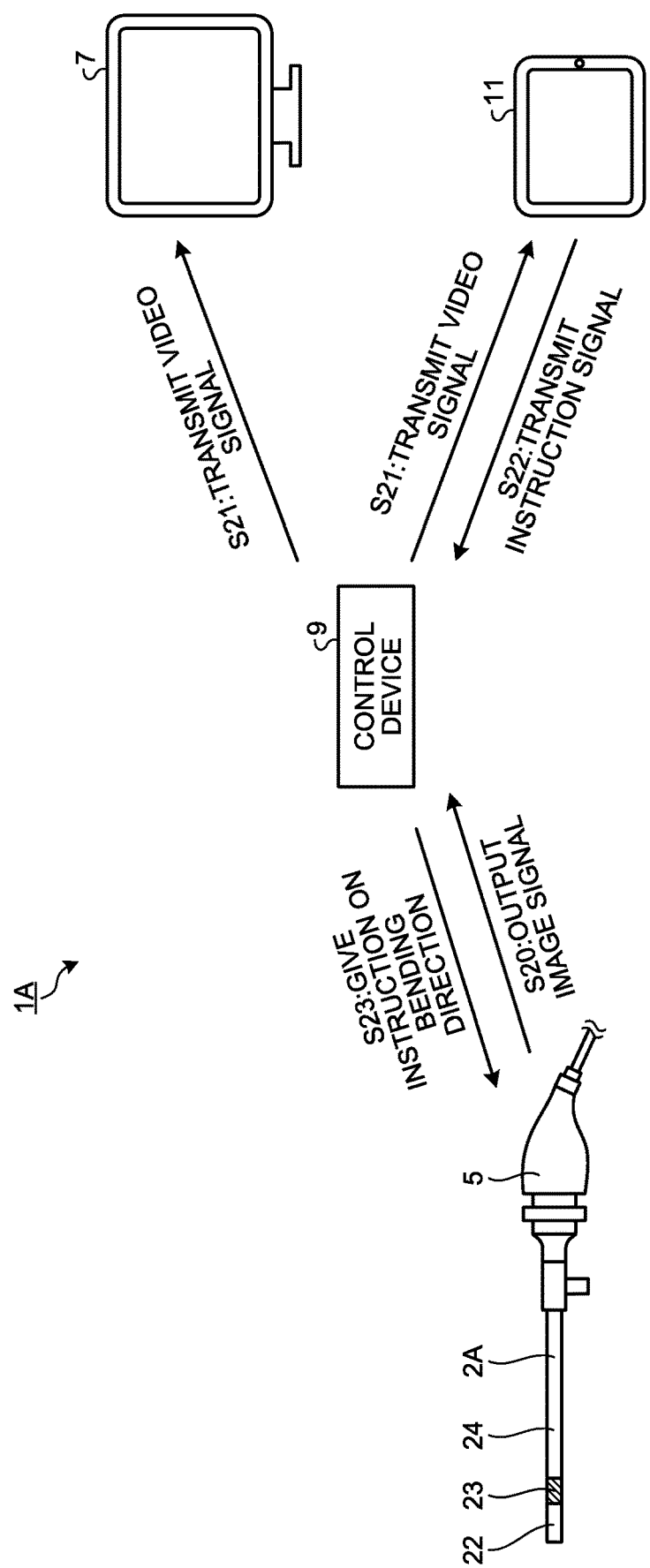
FIG. 19 is a diagram illustrating an outline of processing to be executed by the medical observation system according to the third embodiment.

Next, processing to be executed by the medical observation system 1A will be described. FIG. 19 is a diagram illustrating an outline of the processing to be executed by the medical observation system 1A. Steps S20 and S21 correspond to Steps S1 and S2 in FIG. 3 described above, respectively.

In Step S22, the external device 11 transmits, to the control device 9, an instruction signal to bend the distal end portion 22 of the insertion section 2A at a position where the touch panel 113 has received an input.

Subsequently, the control device 9 drives the bending unit 23 such that the distal end portion 22 of the insertion section 2A is directed to a position corresponding to the instruction signal received from the external device 11 where the touch panel 113 has received the input (Step S23). As a result, the control device 9 can output a display image, obtained by imaging the position touched by a user of the external device 11, to the display device 7.

[Cooperative Processing]

Figure 20:
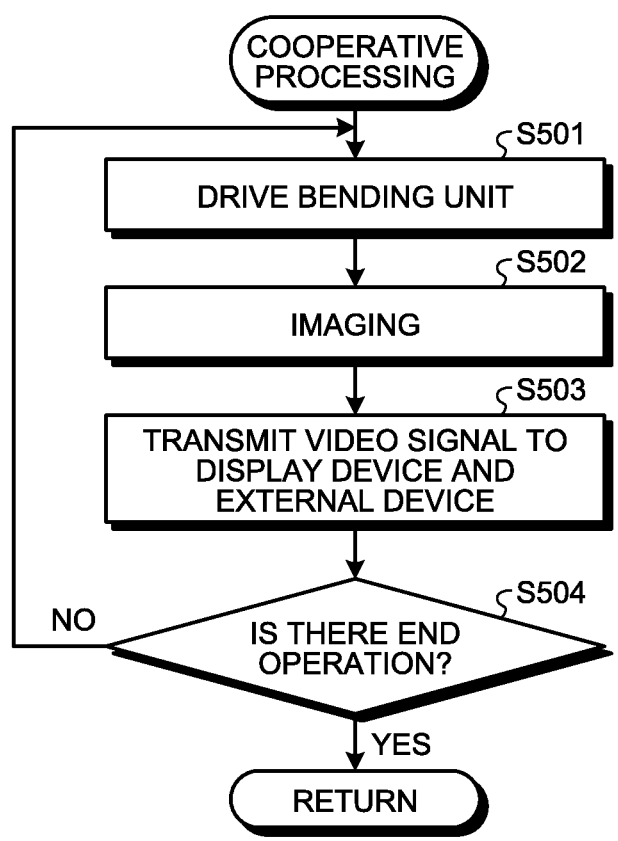
FIG. 20 is a flowchart illustrating an outline of cooperative processing to be executed by the control device according to the third embodiment.

Next, the cooperative processing to be executed by the control device 9 will be described. FIG. 20 is a flowchart illustrating an outline of the cooperative processing to be executed by the control device 9.

As illustrated in FIG. 19, the drive control unit 981 first drives the bending unit 23 such that the distal end portion 22 of the insertion section 2A is directed to the position corresponding to the instruction signal input to the touch panel 113 and received from the external device 11 (Step S501). As a result, an imaging direction can be changed to the position touched by the user of the external device 11. Steps S502 to S504 correspond to Steps S402 to S404 in FIG. 16 described above, respectively. After Step S504, the control device 9 returns to the main routine of FIG. 7 described above.

According to the third embodiment described above, the drive control unit 981 drives the bending unit 23 such that the distal end portion 22 of the insertion section 2A is directed to the position corresponding to the instruction signal received from the external device 11 where the touch panel 113 has received the input, and thus, it is possible to change an observation direction of the insertion section 2A (endoscope) to a position desired by an operator even under a situation where the operator's hand is not available.

Incidentally, the insertion section 2A (endoscope) that can be bent in the vertical and horizontal directions has been described in the third embodiment, but the invention is also applicable to a videoscope-type endoscope in which the insertion section 2A and the camera head 5 are integrated and a field-of-view direction of a distal end can be changed. In addition, the invention is also applicable to other devices as long as the observation direction can be changed. For example, the invention is also applicable to a scope holder that holds the above-described insertion section 2 of the first embodiment to be movable in the vertical and horizontal directions, the front-rear direction, and the rotational direction. In this case, when the drive control unit 981 controls a drive unit of the scope holder according to a position corresponding to an instruction signal received from the external device 11 where the touch panel 113 has received an input, it is possible to change the observation direction of the insertion section 2 (endoscope) to a position desired by an operator even under a situation where the operator's hand is not available. It is a matter of course that a plurality of actuators provided in a manipulator, other than the scope holder, may be controlled according to a position corresponding to an instruction signal received from the external device 11 where the touch panel 113 has received an input.

Fourth Embodiment

Next, a fourth embodiment will be described. Although the invention is applied to the medical observation system 1 using the rigid endoscope (insertion section 2) in the first embodiment described above, the invention is applied to a medical observation system using a surgical microscope, which enlarges and captures a predetermined field-of-view area in an inside of a subject (an inside of a living body) or a surface of the subject (a surface of the living body), in the fourth embodiment. Incidentally, the similar configurations with those of the medical observation system 1 according to the first embodiment described above will be denoted by the same reference signs, and descriptions thereof will be omitted or simplified in the following description.

[Schematic Configuration of Medical Observation System]

Figure 21:
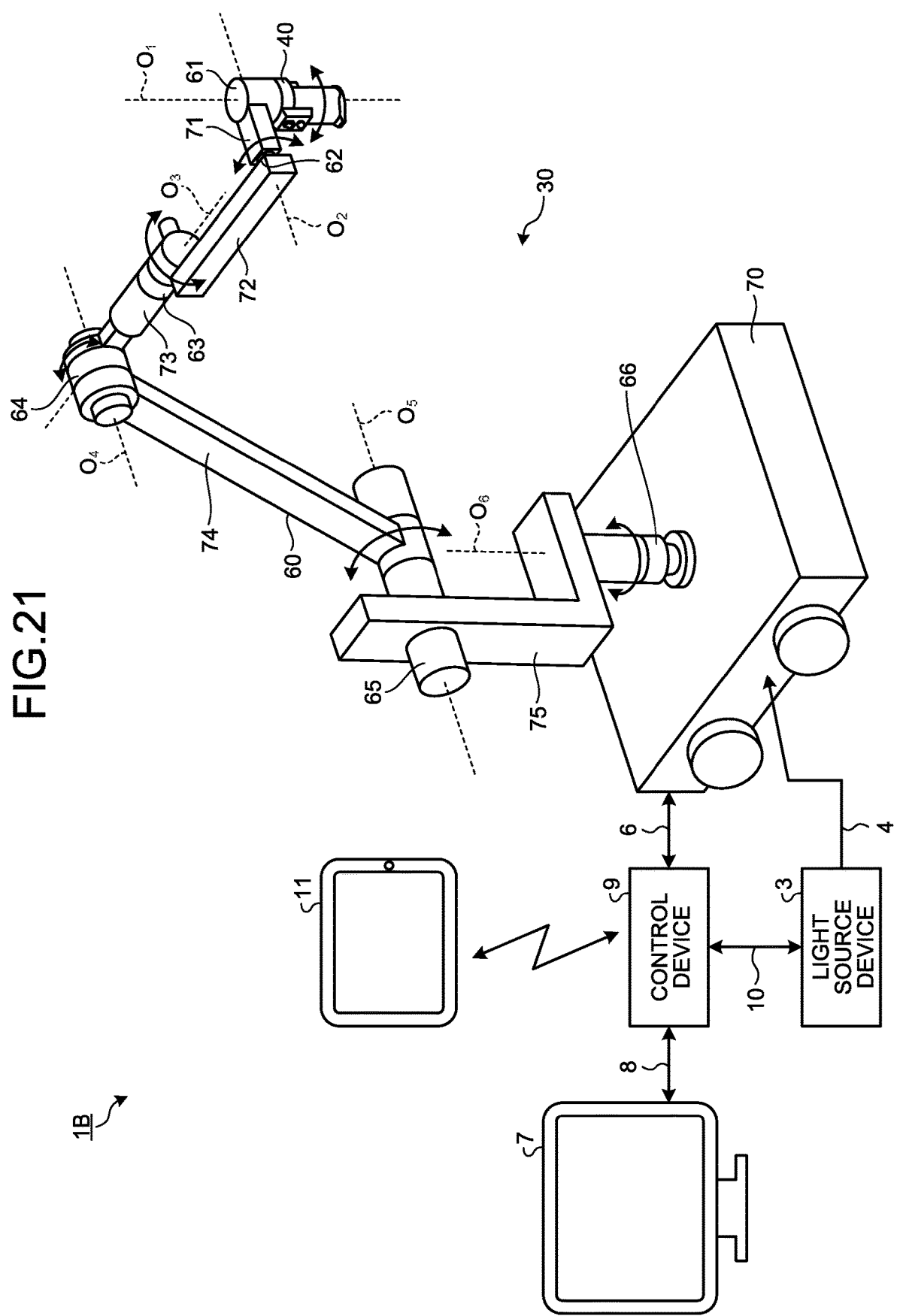
FIG. 21 is a diagram illustrating a schematic configuration of a medical observation system according to a fourth embodiment.

FIG. 21 is a diagram illustrating a schematic configuration of the medical observation system according to the fourth embodiment. A medical observation system 1B illustrated in FIG. 21 includes the light source device 3, the light guide 4, the first transmission cable 6, the display device 7, and the second transmission cable 8, the control device 9, the third transmission cable 10, the external device 11, and an observation device 30.

[Schematic Configuration of Microscope Device]

The observation device 30 illustrated in FIG. 21 is a medical surgical microscope device having a function as a microscope that enlarges and observes a microscopic part of an object to be observed. The observation device 30 includes: a microscope unit 40 which observes the microscopic part of the object to be observed; a support unit 60 which is connected with a proximal end portion of the microscope unit 40 and rotatably supports the microscope unit 40; and a base unit 70 which rotatably holds a proximal end portion of the support unit 60 and is movable on a floor.

The microscope unit 40 includes: an optical system which has a cylindrical appearance and has a zoom function and a focus function inside thereof; an imaging element (not illustrated) which receives a subject image formed by the optical system and performs photoelectric conversion to generate an image signal; and a light-emitting unit (not illustrated) which emits illumination light to the object to be observed. In addition, various switches constituting an input unit that receives an input of an operation instruction of the observation device 30 are provided on a side surface of the microscope unit 40. A cover glass (not illustrated) is provided in an aperture surface of a lower end portion of the microscope unit 40 to protect the internal optical system and the like. A user such as an operator moves the microscope unit 40, changes an angle of the microscope unit 40, changes a mode of the observation device 30, or performs a zoom or focus operation while operating the various switches in the state of gripping the microscope unit 40. Thus, the user can intuitively grasp a direction of an optical axis of the optical system or a central direction of an imaging field of view of the microscope unit 40, and can easily move the microscope unit 40 to a desired position. Incidentally, a shape of the microscope unit 40 is not limited to the cylindrical shape, and may be, for example, a polygonal cylindrical shape.

In the support unit 60, a first joint 61, a first arm 71, a second joint 62, a second arm 72, a third joint 63, a third arm 73, a fourth joint 64, a fourth arm 74, a fifth joint 65, a fifth arm 75, and a sixth joint 66 are connected in this order from a distal end side (the microscope unit 40 side).

The first joint 61 holds the microscope unit 40 on the distal end side to be rotatable about a first axis $O_1$ that coincides with the optical axis of the microscope unit 40, and is held by the first arm 71 in the state of being fixed to a distal end portion of the first arm 71 on a proximal end side.

The second joint 62 holds the first arm 71 to be rotatable about the second axis $O_2$ orthogonal to the first axis $O_1$ on the distal end side, and is held by the second arm 72 on the proximal end side. Similarly, the third joint 63 to the sixth joint 66 rotatably hold the second arm 72 to the fourth arm 74, respectively, on the distal end side, and are held in the state of being fixed to distal end portions of the third arm 73 to the fifth arm 75, respectively, on the proximal end side.

The sixth joint 66 rotatably holds the fifth arm 75 on the distal end side, and is held in the state of being fixed to the base unit 70 on the proximal end side.

The second arm 72 to the fifth arm 75 are rotatable about a third axis $O_3$ to a sixth axis $O_6$, respectively. Each of the fourth axis $O_4$ and the fifth axis $O_5$ is parallel to the second axis $O_2$. The third axis $O_3$ is orthogonal to the fourth axis $O_4$, and the fifth axis $O_5$ is orthogonal to the sixth axis $O_6$.

Each of the first joint 61 to sixth joint 66 has an electromagnetic brake (not illustrated), which prohibits each rotation of the microscope unit 40 and the first arm 71 to the fifth arm 75 on the distal end side, and an angle sensor (not illustrated) which functions as a detection unit. The electromagnetic brake is released in response to a release instruction that the input unit (not illustrated) of the microscope unit 40 receives an input. When the electromagnetic brake is released, the microscope unit 40 and the first arm 71 to the fifth arm 75 become rotatable with respect to the first joint 61 to the sixth joint 66, respectively. Hereinafter, a state where the microscope unit 40 and the first arm 71 to the fifth arm 75 are rotatable with respect to the first joint 61 to the sixth joint 66, respectively, is referred to as an all free mode. Incidentally, an air brake may be applied instead of the electromagnetic brake.

The first joint 61 to the sixth joint 66 are provided with actuators (not illustrated) to assist each rotation of the microscope unit 40 and the first arm 71 to the fifth arm 75. In addition, the first joint 61 to the sixth joint 66 are provided with various sensors (not illustrated) which function as detection units to detect at least some of a position, velocity, an acceleration, a rotational angle, a rotational speed, a rotational acceleration, a generated torque, and the like of each joint.

The support unit 60 having the above configuration realizes motions of six degrees of freedom in total including three translational degrees of freedom and three rotational degrees of freedom in the microscope unit 40.

Figure 22:
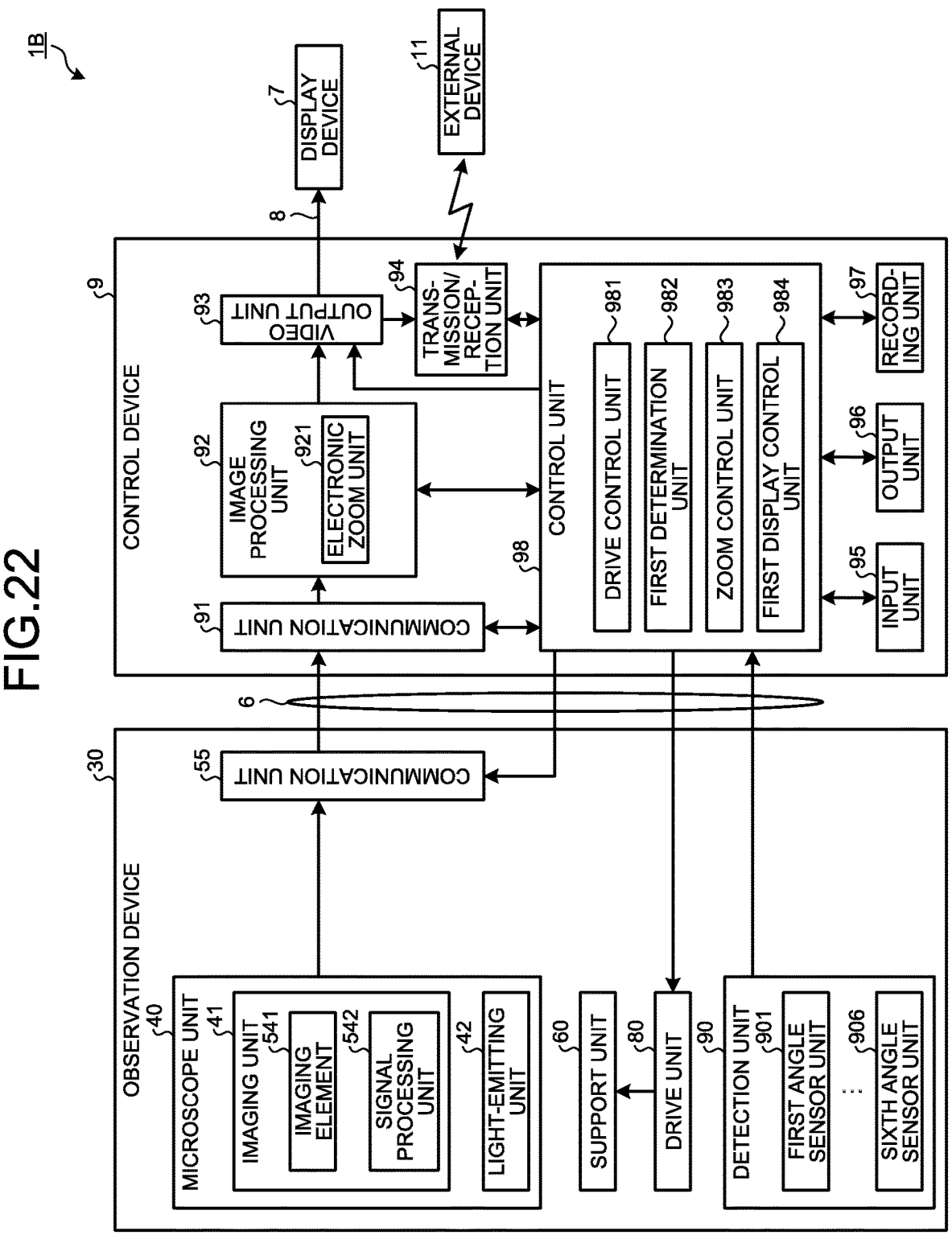
FIG. 22 is a block diagram illustrating functional configurations of an observation device and a control device included in the medical observation system according to the fourth embodiment.

Next, the functional configuration of the observation device 30 will be described. FIG. 22 is a block diagram illustrating the functional configurations of the observation device 30 and the control device 9 included in the medical observation system 1B. Incidentally, FIG. 22 does not illustrate the connectors CN1 and CN2 between the observation device 30 and the control device 9 and the first transmission cable 6, and functional configurations of the light source device 3, the display device 7, and the external device 11 for convenience of the description.

[Functional Configuration of Observation Device]

The functional configuration of the observation device 30 will be described.

The observation device 30 includes at least the microscope unit 40, the communication unit 55, the support unit 60, a drive unit 80, and a detection unit 90 as illustrated in FIG. 22.

The microscope unit 40 includes: an imaging unit 41 that enlarges and captures an image of an object to be observed, which is a subject, to generate an image signal; and a light-emitting unit 42 that irradiates the object to be observed with illumination light supplied from the light source device 3.

The imaging unit 41 includes: an optical system which has zoom and focus functions; the imaging element 541 which receives an image of the object to be observed formed by the optical system and performs photoelectric conversion to generate an image signal; and the signal processing unit 542. An imaging signal generated by the imaging element 541 is transmitted to the control device 9 via the first transmission cable 6. Incidentally, an optical signal may be transmitted to the control device 9 by performing E/O conversion on the imaging signal generated by the imaging element 541.

The light-emitting unit 42 has an illumination optical system configured using one or more lenses. The light-emitting unit 42 emits the illumination light supplied from the light source device 3 via the light guide 4 in the same direction as an imaging direction of the imaging unit 41. Incidentally, light transmission of the light guide 4 and the light source device 3 may be omitted in the light-emitting unit 42 by providing the microscope unit 40 with a Light emitting diode (LED), a laser light source, or the like.

The support unit 60 rotatably supports the microscope unit 40 as illustrated in FIG. 21 described above. The support unit 60 realizes motions of six degrees of freedom in total including three translational degrees of freedom and three rotational degrees of freedom in the microscope unit 40.

The drive unit 80 includes the electromagnetic brake and the actuator provided to each of the first joint 61 to the sixth joint 66 described above. The electromagnetic brake is released in accordance with the release instruction that the input unit receives an input during an operation in the all free mode. The actuator operates according to a control signal transmitted from the control device 9 to be described later based on a state detection result by the detection unit 90.

The detection unit 90 sequentially detects state information of the observation device 30. The state information of the observation device 30 includes information on a position, a focus, and a zoom of the imaging unit 41, information on at least some of positions, velocity, accelerations, rotational angles, rotational speeds, rotational accelerations, and generated torques of the first to sixth joints 61 to 66, information on at least some of positions, velocity, and accelerations of the first arm 71 to the fifth arm 75, and information on operations such as a field-of-view movement mode (pivot operation mode) and the all free mode. The detection unit 90 has various sensors to detect such types of information. Specifically, the detection unit 90 includes first angle sensor unit 901 to sixth angle sensor unit 906 that respectively detect angles of the first arm 71 to the fifth arm 75 (the first axis $O_1$ to the sixth axis $O_6$) with respect to a reference direction. Here, the reference direction is a gravity direction (vertical direction) when a case where the observation device 30 (the first arm 71 to the fifth arm 75) is installed on the floor is set as a reference. That is, the fourth embodiment will be described assuming that the reference direction is 0 degrees. It is a matter of course that the reference direction changes depending on an installation place of the observation device 30 (the first arm 71 to the fifth arm 75). For example, in a case where the installation place of the observation device 30 (the first arm 71 to the fifth arm 75) is a ceiling suspension, the reference direction is different, by 180 degrees, from that in the case of the floor installation. In addition, in a case where the installation place of the observation device 30 (the first arm 71 to the fifth arm 75) is fixed to a wall (fixed to a vertical wall), the reference direction is different, by 90 degrees, from that in the case of the floor installation. Incidentally, when a direction of the first axis $O_1$ detected by the first angle sensor unit 901 and the imaging direction of the imaging unit 41 are the same, the first angle sensor unit 901 may be omitted.

Here, the field-of-view movement mode (pivot operation mode) is a pivot operation in which the microscope unit 40 moves by the movement of the support unit 60 on a conical surface with one point at the top in the state of being fixed at the one point in a central direction of the imaging field of view of the imaging unit 41, and is also called a point lock operation. A pivot axis of the field-of-view movement mode is a central axis in a height direction of a cone. In the field-of-view movement mode, a distance between the fixed point and the imaging unit 41 is kept constant. At the time of surgery, for example, a surgical site is selected as the above-described fixed point. According to the above field-of-view movement mode, the surgical site can be observed equidistantly from different angles, and thus, a user can grasp the surgical site more accurately.

[Processing of Medical Observation System]

Figure 23:
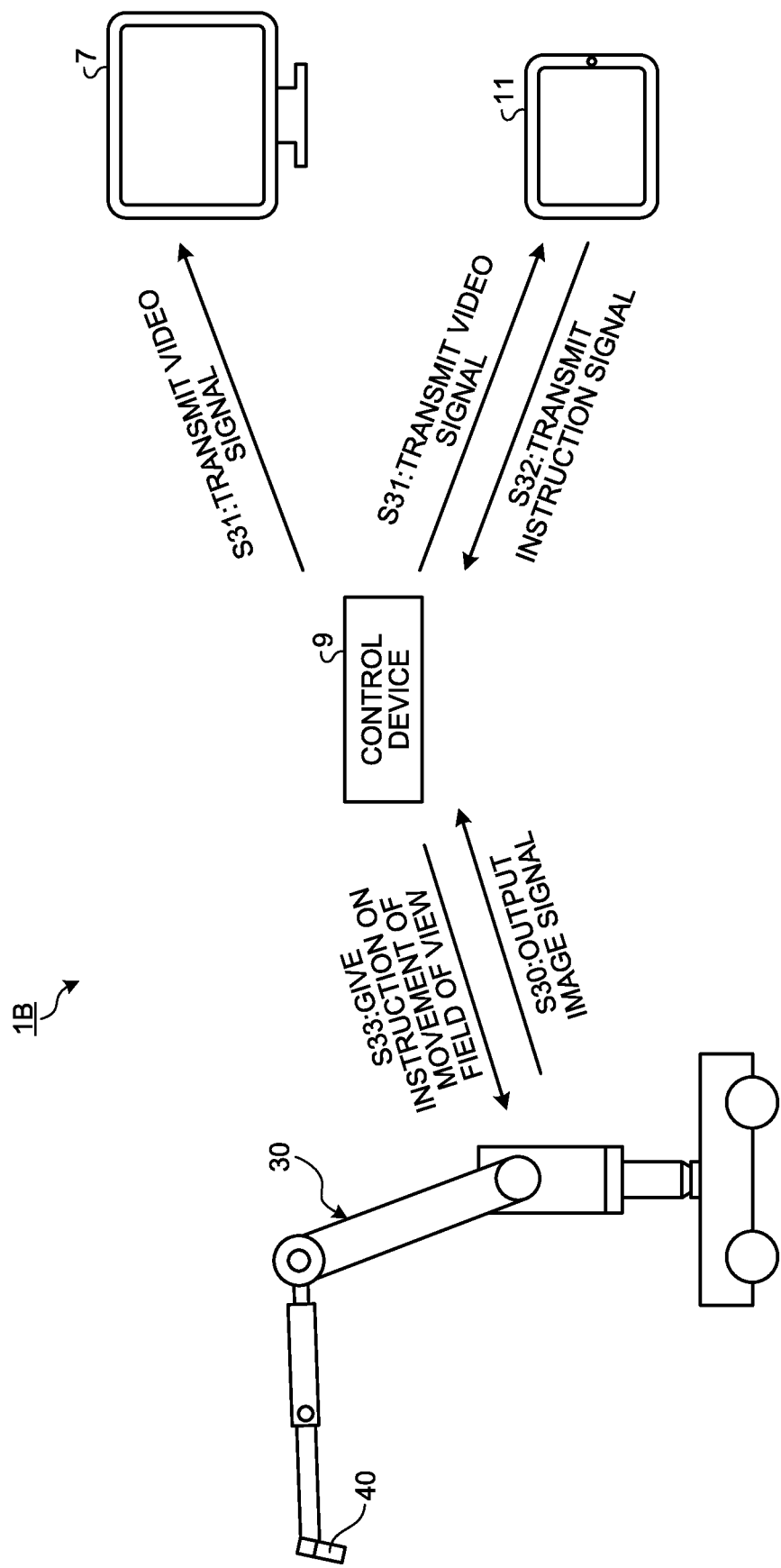
FIG. 23 is a diagram illustrating an outline of processing to be executed by the medical observation system according to the fourth embodiment.

Next, processing to be executed by the medical observation system 1B will be described. FIG. 23 is a diagram illustrating an outline of the processing to be executed by the medical observation system 1B. Steps S30 and S31 correspond to Steps S1 and S2 in FIG. 3 described above, respectively.

In Step S32, the external device 11 transmits an instruction signal to the control device 9 such that a position where the touch panel 113 has received an input become a center of an observation field of view of the microscope unit 40.

Subsequently, the drive unit 80 is driven such that the center of the observation field of view of the microscope unit 40 is directed to the position corresponding to the instruction signal received from the external device 11 where the touch panel 113 has received the input, thereby moving the field of view of the microscope unit 40 via the support unit 60 (Step S33). As a result, the control device 9 can direct the center of the observation field of view of the microscope unit 40 to the position touched by the user of the external device 11.

[Cooperative Processing]

Figure 24:
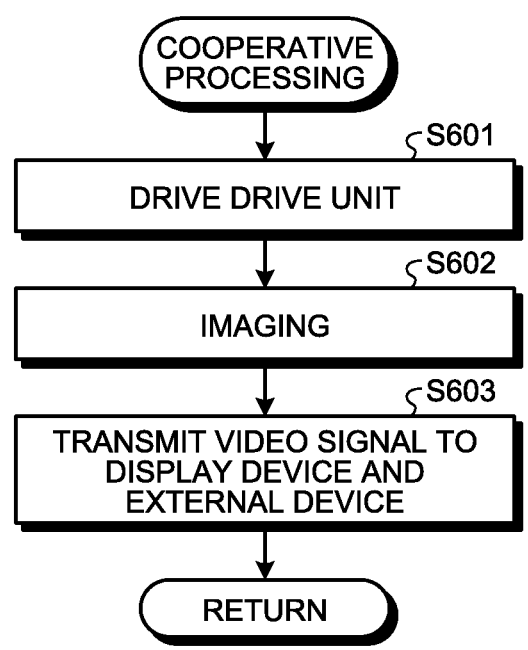
FIG. 24 is a flowchart illustrating an outline of cooperative processing to be executed by the control device according to the fourth embodiment.

Next, the cooperative processing to be executed by the control device 9 will be described. FIG. 24 is a flowchart illustrating an outline of the cooperative processing to be executed by the control device 9.

As illustrated in FIG. 24, the drive control unit 981 first drives the drive unit 80 to move the support unit 60 such that the center of the observation field of view of the microscope unit 40 is located at the touch position corresponding to the instruction signal received from the external device 11 where the touch panel 113 has received the input, thereby moving the field of view of the microscope unit 40 such that the center of the imaging field of view of the microscope unit 40 is directed to the touch position (Step S601). As a result, it is possible to align the center of the observation field of view of the microscope unit 40 to the position touched by the user of the external device 11. Steps S602 and S603 correspond to Steps S402 and S403 in FIG. 16 described above, respectively. After Step S603, the control device 9 returns to the main routine of FIG. 7 described above.

According to the fourth embodiment described above, the field of view of the microscope unit 40 is moved as the drive control unit 981 drives the drive unit 80 to move the support unit 60 such that the center of the observation field of view of the microscope unit 40 is directed to the position corresponding to the instruction signal received from the external device 11 where the touch panel 113 has received the input, and thus, it is possible to move the observation field of view of the microscope unit 40 to a position desired by an operator even under a situation where the operator's hand is not available. It is a matter of course that the drive control unit 981 may drive the drive unit 80 to move the support unit 60 such that the center of the observation field of view of the microscope unit 40 coincides with the position corresponding to the instruction signal received from the external device 11 where the touch panel 113 has received the input.

In addition, the drive control unit 981 moves the field of view of the microscope unit 40 to the touch position corresponding to the instruction signal received from the external device 11 where the touch panel 113 has received the input in the fourth embodiment, but the invention is not limited thereto, and a mode of the observation device 30 may be changed. In this case, the drive control unit 981 may change the mode of the observation device 30 based on the touch position included in the instruction signal received from the external device 11 where the touch panel 113 has received the input and trajectory information of touch positions. For example, the drive control unit 981 may set the mode of the observation device 30 to the field-of-view movement mode when a trajectory of touch positions draws a circle, and may set the mode of the observation device 30 to the all free mode when the trajectory of touch positions draws a polygon.

Other Embodiments

Although the context of each step has been clearly described using expressions such as "first", "thereafter", "subsequently", and "then" in the description of the treatment of the medical observation system in the present specification, the order of steps required to implement the embodiments is not uniquely defined by those expressions. That is, the order of the medical observation system described in the present specification can be changed within a range causing no contradiction.

In addition, the present invention is not limited directly to the above embodiments, and the components thereof can be modified and embodied within a scope not departing from a gist of the invention in the implementation stage. In addition, various inventions can be formed by appropriately combining a plurality of components disclosed in the above-described embodiments. For example, some components may be deleted from all the components described in the above-described embodiments. Further, the components described in the respective embodiments may be combined as appropriate.

In addition, the terms described together with broader or synonymous different terms at least once in the specification or the drawings can be replaced with the different terms anywhere in the specification or the drawings. In this manner, various modifications and applications are possible within the scope not departing from the gist of the invention.

In this manner, the present invention may include various embodiments not described herein, and various design changes can be made within a scope of a technical idea specified by the claims.

REFERENCE SIGNS LIST 1, 1A, 1B MEDICAL OBSERVATION SYSTEM
2, 2A INSERTION SECTION
3 LIGHT SOURCE DEVICE
4 LIGHT GUIDE
5 CAMERA HEAD
6 FIRST TRANSMISSION CABLE
7 DISPLAY DEVICE
8 SECOND TRANSMISSION CABLE
9 CONTROL DEVICE
10 THIRD TRANSMISSION CABLE
11 EXTERNAL DEVICE
22 DISTAL END PORTION
23 BENDING UNIT
24 BODY SECTION
25 OPTICAL SYSTEM
30 OBSERVATION DEVICE
40 MICROSCOPE UNIT
41, 54 IMAGING UNIT
42 LIGHT-EMITTING UNIT
51 LENS UNIT
52 LENS DRIVE UNIT
60 SUPPORT UNIT
80 DRIVE UNIT
92 IMAGE PROCESSING UNIT
93 VIDEO OUTPUT UNIT 94, 111 TRANSMISSION/RECEPTION UNIT
98 CONTROL UNIT
112 DISPLAY UNIT
113 TOUCH PANEL
114 INPUT UNIT
115 RECORDING UNIT
116 DEVICE CONTROL UNIT
116a SECOND DETERMINATION UNIT
116b SECOND DISPLAY CONTROL UNIT
116c COMMUNICATION CONTROL UNIT
511 FOCUS LENS
512 ZOOM LENS
541 IMAGING ELEMENT
542 SIGNAL PROCESSING UNIT
921 ELECTRONIC ZOOM UNIT
981 DRIVE CONTROL UNIT
982 FIRST DETERMINATION UNIT
983 ZOOM CONTROL UNIT
984 FIRST DISPLAY CONTROL UNIT

The invention claimed is:

1. A control device comprising:
an image processor configured to process an image signal generated by a camera to generate a live-view image;
a video output configured to output the live-view image generated by the image processor to a first display;
a transceiver configured to transmit the live-view image generated by the image processor to an external device including a second display, which is capable of bidirectional communication, and receive an instruction signal including at least one touch position in the live-view image from the external device; and
a control circuitry configured to
determine whether a first touch area including the at least one touch position has a predetermined resolution or higher,
on condition that the first touch area has the predetermined resolution or higher, generate an enlarged image on the first touch area,
on condition that the first touch area has less than the predetermined resolution, change the first touch area to a second touch area including the at least one touch position, the second touch area having the predetermined resolution or higher, and generate an enlarged image on the second touch area, and
cause the video output to output the enlarged image to the first display.

2. The control device according to claim 1, wherein
the control circuitry is configured to:
determine whether the touch area including the touch position has a predetermined resolution or higher; and
change a touch area to be enlarged to include the touch position in the live-view image on condition that the touch area including the touch position is not the predetermined resolution or higher.

3. The control device according to claim 2, wherein
the instruction signal further includes two of the at least one touch positions different from each other, and
the control circuitry is configured to change a size of a touch area to be enlarged according to a distance between the two touch positions.

4. The control device according to claim 1, wherein
effective number of pixels of the camera is eight megapixels or more,
the first display has a monitor size of 31 inches or more, and
the control circuitry is configured to generate the enlarged image having a resolution of two megapixels or more.

5. The control device according to claim 1, wherein
the instruction signal further includes trajectory information of the touch position moving with a lapse of time,
the live-view image includes a subject image and a mask area other than the subject image, and
the control circuitry is configured to cause the video output to change a display position of the subject image based on the trajectory information and output the subject image to the first display.

6. The control device according to claim 1, wherein
the control circuitry is configured to control a lens driver that adjusts a focus by moving one or more lenses, to be focused at a position of the live-view image according to the instruction signal.

7. The control device according to claim 1, wherein
the control circuitry is configured to control a bending area in an endoscope, which includes a distal end portion provided with the camera, wherein the bending area can be bent at the distal end portion in vertical and horizontal direction s toward a position of the first display according to the instruction signal.

8. The control device according to claim 1, wherein
the control circuitry is configured to control a support, configured to movably hold at least the camera, to cause a center of an imaging field of view in the camera to be directed to the touch position of the live-view image according to the instruction signal.

9. An external device including a second display comprising:
a display area configured to display a live-view image corresponding to an image signal transmitted from a camera through a control circuit; and
a touch panel overlapping the display area, the touch panel being configured to detect a touch position at which an external object comes in contact with the touch panel, and to output an instruction signal including the touch position; and
a display control circuit configured to display area information indicating a touch area, which includes the touch position and satisfies a predetermined resolution, on the display area to be superimposed on the live-view image based on the instruction signal output from the touch panel;
the display control circuit configured to
determine whether a first touch area including the at least one touch position has a predetermined resolution or higher,
on condition that the first touch area has the predetermined resolution or higher, generate an enlarged image on the first touch area,
on condition that the first touch area has less than the predetermined resolution, change the first touch area to a second touch area including the at least one touch position, the second touch area having the predetermined resolution or higher, and generate an enlarged image on the second touch area, and
cause the video output to output the enlarged image to a first display.

10. The external device including the second display according to claim 9 further comprising
the display control circuit is configured to determine whether the touch area including the touch position has a predetermined resolution or higher, wherein the display control circuit is configured to change a superimposed position of the area information so as to include the touch position when the touch area including the touch position is not the predetermined resolution or higher, and display the area information on the display area.

11. A medical observation system comprising:
an image processor configured to process an image signal generated by a camera to generate a live-view image for display;
a video output configured to output the live-view image generated by the image processor to a second display;
a transceiver configured to transmit the live-view image to and receive information from an external device including the second display including:
a display area configured to display the live-view image transmitted from the transceiver, and
a touch panel superimposed on the display area of the touch panel being configured to detect touch positions at which an external object comes in contact, and output an instruction signal including at least one of the touch positions; and
a control circuitry configured to generate an enlarged image on a touch area including the at least one touch position from the external device including the second display; and
the control circuitry configured to
determine whether a first touch area including the at least one touch position has a predetermined resolution or higher,
on condition that the first touch area has the predetermined resolution or higher, generate an enlarged image on the first touch area,
on condition that the first touch area has less than the predetermined resolution, change the first touch area to a second touch area including the at least one touch position, the second touch area having the predetermined resolution or higher, and generate an enlarged image on the second touch area, and
cause the video output to output the enlarged image to a first display.

12. A control method comprising:
processing an image signal generated by a camera to generate a live-view image transmitting the processed live-view image to each of a first display and an external device including a second display which has a display function and is capable of bidirectional communication;
receiving an instruction signal including at least one touch position in the live-view image from the external device including the second display; and
generating an enlarged image on a touch area including the at least one touch position according to the instruction signal from the external device including the second display; and
determining whether a first touch area including the at least one touch position has a predetermined resolution or higher,
on condition that the first touch area has the predetermined resolution or higher, generating an enlarged image on the first touch area,
on condition that the first touch area has less than the predetermined resolution, changing the first touch area to a second touch area including the at least one touch position, the second touch area having the predetermined resolution or higher, and generate an enlarged image on the second touch area, and
causing the video output to output the enlarged image to the first display.

13. A display method executed by an external device including a second display including:
a display area that displays a live-view image corresponding to an image signal transmitted from a control circuit; and
a touch panel that overlaps the display area detects a touch position at which an external object comes in contact, and outputs an instruction signal including the touch position, the display method comprising
displaying area information indicating a touch area, which includes the touch position and satisfies a predetermined resolution, on the display area to be superimposed on the live-view image: based on the instruction signal output from the touch panel; and
the control circuit configured to
determine whether a first touch area including the touch position has a predetermined resolution or higher,
on condition that the first touch area has the predetermined resolution or higher, generate an enlarged image on the first touch area,
on condition that the first touch area has less than the predetermined resolution, change the first touch area to a second touch area including the touch position, the second touch area having the predetermined resolution or higher, and generate an enlarged image on the second touch area, and
cause the video output to output the enlarged image to a first display.

14. A non-transitory computer-readable medium that causes a control device to execute a stored program:
processing an image signal generated by a camera to generate a live-view image; transmitting the processed live-view image to each of a first display and an external device including a second display which has a display function and is capable of bidirectional communication;
receiving an instruction signal including at least one touch position in the live-view image from the external device including the second display; and
generating an enlarged image on a touch area including the at least one touch position according to the instruction signal from the external device; and
determining whether a first touch area including the second display the at least one touch position has a predetermined resolution or higher,
on condition that the first touch area has the predetermined resolution or higher, generating an enlarged image on the first touch area,
on condition that the first touch area has less than the predetermined resolution, changing the first touch area to a second touch area including the at least one touch position, the second touch area having the predetermined resolution or higher, and generate an enlarged image on the second touch area, and
causing the video output to output the enlarged image to the first display.

15. A non-transitory computer-readable medium that causes an external device including a second display to execute a stored program, wherein the external device includes:
a display area that displays a live-view image corresponding to an image signal transmitted from a control circuit; and
a touch panel that overlaps the display area, detects a touch position at which an external object comes in contact, and outputs an instruction signal including the touch position, to execute displaying area information indicating a touch area, which includes the touch position and satisfies a predetermined resolution, on the display area to be superimposed on the live-view image based on the instruction signal output from the touch panel; and the control circuit configured to determine whether a first touch area including the touch position has a predetermined resolution or higher, on condition that the first touch area has the predetermined resolution or higher, generate an enlarged image on the first touch area, on condition that the first touch area has less than the predetermined resolution, change the first touch area to a second touch area including the at least one touch position, the second touch area having the predetermined resolution or higher, and generate an enlarged image on the second touch area, and cause the video output to output the enlarged image to a first display.

16. The program according to claim 15, further comprising:

transmitting the instruction signal to the control circuit, the control circuit being configured to enlarge the touch area and to output the enlarged area on the first display separate from the display area of the external device including the second display.

17. The external device including the second display according to claim 9, further comprising: wherein the display control circuit is configured to transmit the instruction signal to the control circuit, the control circuit being configured to enlarge the touch area and to output the enlarged area on the first display separate from the display area of the external device including the second display.

18. The display method according to claim 13, further comprising:

transmitting the instruction signal to the control circuit, the control circuit being configured to enlarge the touch area and to output the enlarged area on the first display separate from the display area of the external device including the second display.

* * * * *